(12) United States Patent
Tayebi et al.

(10) Patent No.: US 12,076,422 B2
(45) Date of Patent: Sep. 3, 2024

(54) MEDICAL AND DENTAL INTEGRATED MULTIPHASIC BIOMATERIALS FOR SINGLE OR MULTI-TISSUE RECONSTRUCTION/REGENERATION

(71) Applicant: Marquette University, Milwaukee, WI (US)

(72) Inventors: Lobat Tayebi, Milwaukee, WI (US); Erfan Dashtimoghadam, Milwaukee, WI (US); Farahnaz Fahimipour, Milwaukee, WI (US)

(73) Assignee: Marquette University, Milwaukee, WI (US)

(*) Notice: Subject to any disclaimer, the term of this patent is extended or adjusted under 35 U.S.C. 154(b) by 639 days.

(21) Appl. No.: 16/612,328

(22) PCT Filed: May 10, 2018

(86) PCT No.: PCT/US2018/032084
§ 371 (c)(1),
(2) Date: Nov. 8, 2019

(87) PCT Pub. No.: WO2018/209101
PCT Pub. Date: Nov. 15, 2018

(65) Prior Publication Data
US 2021/0077359 A1  Mar. 18, 2021

Related U.S. Application Data

(60) Provisional application No. 62/504,198, filed on May 10, 2017.

(51) Int. Cl.
| A61K 6/17 | (2020.01) |
| A61K 6/54 | (2020.01) |
| A61K 6/831 | (2020.01) |
| A61K 6/884 | (2020.01) |
| A61L 27/26 | (2006.01) |
| C12N 5/0775 | (2010.01) |

(52) U.S. Cl.
CPC .................. *A61K 6/54* (2020.01); *A61K 6/17* (2020.01); *A61K 6/831* (2020.01); *A61K 6/884* (2020.01); *A61L 27/26* (2013.01); *C12N 5/0662* (2013.01); *C12N 2533/40* (2013.01)

(58) Field of Classification Search
CPC .......... A61K 6/54; A61K 6/884; A61K 6/831; A61K 6/17; A61L 27/26; C12N 5/0662; C12N 2533/40
See application file for complete search history.

(56) References Cited

U.S. PATENT DOCUMENTS

| 4,587,284 A | 5/1986 | Lueissi |
| 4,970,298 A * | 11/1990 | Silver .................. A61L 27/58 |
| | | 523/105 |
| 5,415,547 A | 5/1995 | Torabinejad |
| 5,769,638 A | 6/1998 | Torabinejad |
| 5,837,278 A | 11/1998 | Geistlich |
| 6,221,109 B1 | 4/2001 | Geistlich |
| 6,576,015 B2 | 6/2003 | Geistlich |
| 6,713,085 B2 | 3/2004 | Geistlich |
| 6,752,834 B2 | 6/2004 | Geistlich |
| 8,460,691 B2 | 6/2013 | Lauritzen |
| 2006/0067969 A1 | 3/2006 | Lu |
| 2009/0280179 A1 | 11/2009 | Neumann |
| 2010/0190254 A1 | 7/2010 | Chian |
| 2010/0292791 A1 | 11/2010 | Lu |
| 2011/0270394 A1 | 11/2011 | Herford |
| 2015/0297798 A1 | 10/2015 | Badylak |
| 2019/0062462 A1 * | 2/2019 | Shi .................. A61L 27/20 |

FOREIGN PATENT DOCUMENTS

| CN | 106377797 A * | 2/2017 | ............. A61L 27/18 |
| WO | 2005056708 A2 | 6/2005 | |
| WO | WO-2005056708 A2 * | 6/2005 | ........... A61K 9/0004 |
| WO | WO-2008051881 A2 * | 5/2008 | ............. A61F 2/844 |
| WO | WO-2008154030 A2 * | 12/2008 | ........... A61F 2/0811 |
| WO | 2017192525 A1 | 11/2017 | |
| WO | 2018081213 A1 | 5/2018 | |
| WO | 2018209101 A1 | 11/2018 | |

(Continued)

OTHER PUBLICATIONS

Eunkyung Ko, Kisuk Yang, Jisoo Shin, and Seung-Woo Cho. "Polydopamine-Assisted Osteoinductive Peptide Immobilization of Polymer Scaffolds for Enhanced Bone Regeneration by Human Adipose-Derived Stem Cells," Biomacromolecules 2013, 14, 3202-3213. (Year: 2013).*
Bartold Pm, et al. (2000). Tissue engineering: a new paradigm for periodontal regeneration. Periodontol 2000 24:253-269.
Chen J, et al (2011). Simultaneous regeneration of articular cartilage and subchondral bone in vivo using MSCs induced by a spatially controlled gene delivery system in bilayered integrated scaffolds. Biomaterials 32:4793-4805.
Darby Ib, et al (2013). A systematic review of the use of growth factors in human periodontal regeneration. J Periodontol 84:465-476.
European Patent Office. Extended European Search Report for application 18798138.6. Mailed on Jan. 14, 2021. 6 pages.
Griffith, L.G et al, 2002. Tissue engineering—current challenges and expanding opportunities. Science, 295(5557), pp. 1009-1014.
Harley Ba, et al. (2010). Design of a multiphase osteochondral scaffold: III. Fabrication of layered scaffolds with continuous interfaces. J Biomed Mater Res A 92:1078-1093.

(Continued)

*Primary Examiner* — Michael P Cohen
(74) *Attorney, Agent, or Firm* — Quarles & Brady LLP

(57) ABSTRACT

Disclosed herein are composite materials which may be used as biomedical materials or constructs. The disclosed biomedical materials or constructs may be multiphasic and typically provide a surface for cell growth. The disclosed biomedical materials and constructs typically comprise conjugable and/or adhesive chemical moieties, such as hydroxylated aromatic moieties, which facilitate integration of the components of the biomedical materials and constructs. Suitable hydroxylated aromatic moieties may include dihydroxybenzene (DHB) moieties, such as 1,2-DHB moeities, and derivatives thereof.

17 Claims, 8 Drawing Sheets

(56) References Cited

FOREIGN PATENT DOCUMENTS

WO 2019204404 A1 10/2019

OTHER PUBLICATIONS

Hutmacher, D.W., 2000. Scaffolds in tissue engineering bone and cartilage. Biomaterials, 21(24), pp. 2529-2543.

Hynes K, et al (2012). Clinical utility of stem cells for periodontal regeneration. Periodontol 2000, 59:203-227.

International Searching Authority. International Search Report and Written Opinion for application PCT/US2018/032084. Mailed on Aug. 23, 2018. 10 pages.

Iwata T, et al. (2009). Periodontal regeneration with multi-layered periodontal ligament-derived cell sheets in a canine model. Biomaterials 30:2716-2723.

Ko, E., et al. "Polydopamine-assisted osteoinductive peptide immobilization of polymer scaffolds for enhanced bone regeneration by human adipose-derived stem cells." Biomacromolecules 14.9 (2013): 3202-3213.

Lu, H.H. et al, 2005. Interface Tissue Engineering and the Formulation of Multiple-Tissue Systems. In Tissue Engineering I (pp. 91-111). Springer Berlin Heidelberg.

Park, C.H., et al., 2012. Tissue engineering bone-ligament complexes using fiber-guiding scaffolds. Biomaterials, 33 (1), pp. 137-145.

Wang W, et al. (2010). The restoration of full-thickness cartilage defects with BMSCs and TGF-beta 1 loaded PLGA/fibrin gel constructs. Biomaterials 31:8964-8973.

Williams, R.C., 1990. Periodontal disease. New England Journal of Medicine, 322(6), pp. 373-382.

\* cited by examiner

MEDICAL AND DENTAL INTEGRATED MULTIPHASIC BIOMATERIALS FOR SINGLE OR MULTI-TISSUE RECONSTRUCTION/REGENERATION

CROSS-REFERENCE TO RELATED PATENT APPLICATIONS

The present application is the U.S. national stage entry of International Application No. PCT/US2018/032084 filed May 10, 2018, which application claims the benefit of priority under 35 U.S.C. § 119(e) to U.S. Provisional Application No. 62/504,198, filed on May 10, 2017, the content of which is incorporated herein by reference in its entirety.

BACKGROUND

The field of the invention relates to biomedical compositions and uses thereof in methods for tissue regeneration. In particular, the field of the invention relates to integrated biomedical constructs for use in multi-tissue regeneration which may incorporate therapeutic agents. Application of the disclosed biomedical constructs include, but are not limited to bone-periodontal ligament applications, tooth (cementum)-periodontal ligament applications, dentin-pulp complex applications, bone-mucosa applications, bone-tendon applications, bone-cartilage applications, and bone-ligament applications.

Biomedical constructs for use in tissue regeneration are known in the art. Geistlich Pharma Inc. manufactures a product called Bio-Gide®, which is the leading collagen membrane in North America for oral tissue regeneration. Organogenesis Inc. manufactures a product called PuraPly™ Antimicrobial, in which purified Type 1 native collagen creates a durable biocompatible scaffold and polyhexamethylene molecule biguanide (PHMB) is incorporated to inhibit the formation of biofilm on the wound surface. Biomatlante manufactures a product called EZ Cure™ Membrane, which is a cross-linked collagen membrane that combines resorption control and flexibility, and EZ Cure™ Resorbable Membrane, which is derived from an original extraction process and offers good handling properties. Kayeron manufactures a product called Hemicole Fleece, which is a hemostatic collagen membrane. Botiss Biomaterials manufactures a product called Collprotect® membrane, which is a collagen-based product. Collagens commonly are used in biomedical products because collagens are resistant to non-specific proteolytic degradation and are only degraded by specific enzymes called collagenases. Also, collagens are involved in the primary hemostatic reaction. Thus, collagen-based products such as Collprotect® membrane help to stabilize the wound area and control bleeding and can support wound healing.

Other biomedical products are designed for delivering therapeutic agents. Medtronic manufactures a product called Infuse and Olympus Biosciences manufactures a product called OPI. These products are scaffolds for BMP delivery (BMP-2), which utilize a collagen sponge into which a BMP solution is soaked into prior to implantation.

In addition, other types of biomedical products are useful for wound dressing and healing. Polymem manufactures a product called PolyMem Foam Dressing. Features of the Polymem Non-Adhesive Dressing, include bacteriostatic properties, a foam-like feel which maintains a moist environment, and a wound cleanser and moisturizer. PolyMem Foam Dressing includes a standard hydrophilic polyurethane membrane with a semi-permeable polyurethane continuous thin film backing. Degrapol manufactures a product, Degrapol®, which is a biocompatible and biodegradable polyester-urethane which has elastic and mechanical characteristics depending on the modular fabric to be regenerated or supported. DegraPol® is inserted into a research project in the field of tissue engineering.

Despite the biomedical products known in the art, new biomedical products are desirable. Particularly desirable are integrated biomedical constructs that are suturable for use in multi-tissue regeneration and that may incorporate therapeutic agents.

SUMMARY

Disclosed herein are composite materials which may be used as biomedical materials or constructs. The disclosed biomedical materials or constructs typically provide a surface for cell growth and comprise adhesive or conjugable chemical groups that facilitate incorporation into the biomedical materials of additional structural and/or therapeutic components.

Suitable adhesive chemical groups for the disclosed biomedical materials may include but are not limited to hydroxylated aromatic moieties that facilitate integration of the components of the composite materials. The hydroxylated aromatic moieties may include dihydroxybenzene (DHB) moieties, such as 1,2-DHB moieties, and derivatives thereof, which may provide free hydroxyls that can crosslink the components of the composite materials.

The disclosed biomedical materials may be integrated heterophasic biomedical materials comprising: (1) a supportive phase; and (2) a matrix phase; wherein the supportive phase and/or the matrix phase optionally may comprise chemical adhesive or conjugable groups (e.g. DHB moieties). Optionally, the biomedical materials here may include a third phase which acts as a barrier layer to prohibit or control infiltration of unwanted agents, such as water, cells, and bacteria, and the third phase may comprise and/or may be prepared from polycaprolactone film, and/or collagen film. In the biomedical materials here, DHB moieties may be incorporated into one or more of the phases in a form or manner selected from salt form, as part of polymerized particles, via in-situ polymerization, via photo-polymerization, via functionalization to polymer chains, and via surface modification of particles. Preferably, the incorporated DHB moieties provide adhesion between the phases, improve bioactivity of the constructs and/or provide bioadhesion of the biomedical material to soft/hard tissues.

The disclosed biomedical materials may include a hybrid multiphasic constructs for single or multi-tissue regeneration or healing, where the constructs comprise: (1) a scaffold phase that acts as a supportive phase; and (2) another phase which acts as a biomaterial matrix. Optionally, the biomedical material here may comprise a third phase which acts as a barrier to prohibit or control infiltration of unwanted agents (e.g. water, cells, bacteria) and/or which provides a platform for regeneration of a different desirable tissue. One or more of the phases of the biomedical material here may incorporate the described DHB moieties, for example, to provide adhesion between the phases, improve bioactivity of the constructs and/or provide bioadhesion of the biomedical material to soft/hard tissues.

The disclosed biomedical materials may include a bone/endodontic fitting and/or sealing materials comprising: (1) a liquid phase which functions as a binder phase; and (2) a powder phase which functions as a matrix phase. The biomedical materials here optionally may include a spongy form as a third phase, which optionally is a collagen sponge. DHB moieties here may be incorporated in the liquid phase and/or powder phase in a form or manner selected from salt form, as part of polymerized particles, via in-situ polymerization, via photo-polymerization, via functionalization to polymer chains, and via surface modification of particles. Preferably, the DHB moieties provide adhesion between the phases, improve bioactivity of the constructs and/or provide bioadhesion of the biomedical material to soft/hard tissues.

The disclosed biomedical materials may include a hybrid multiphasic constructs for single or multi-tissue regeneration or healing, where the constructs comprise: (1) a scaffold phase that acts as a supportive phase; and (2) another phase which acts as a biomaterial matrix. Optionally, the biomedical material here may comprise a third phase which acts as a barrier to prohibit or control infiltration of unwanted agents (e.g. water, cells, bacteria) and/or which provides a platform for regeneration of a different desirable tissue. One or more of the phases of the biomedical material here may incorporate the described DHB moieties, for example, to provide adhesion between the phases, improve bioactivity of the constructs and/or provide bioadhesion of the biomedical material to soft/hard tissues.

The disclosed biomedical materials may include microcarrier constructs for dynamic cell expansion in vitro and/or microscaffold constructs for tissue regeneration, where the microcarrier constructs and/or microscaffold constructs comprise microparticles which act as a matrix phase and which may accommodate cells or other bioactive agents. Optionally, the microcarrier constructs and/or microscaffold constructs may comprise a binder phase which comprises and/or is formed from polymeric gels, stimuli-responsive hydrogels, and/or photo-crosslinkable macromonomers/polymers, and which is capable of accommodating therapeutic and/or bioactive molecules (e.g., antibacterial agents, therapeutic drugs, growth factors) via immobilization, conjugation, and/or encapsulation. The microcarrier constructs and/or microscaffold constructs may incorporate the DHB moieties in a form or manner selected from salt form, polymerized particle form, via in-situ polymerization, via photo-polymerization, via functionalization of polymer chains forming the phase, and via surface modification. Preferably, the DHB moieties aid in integration of the microcarrier constructs and/or microscaffold constructs, improve bioactivity of the microcarrier constructs and/or microscaffold constructs and/or provide for bioadhesion of the microcarrier constructs and/or microscaffold constructs to soft/hard tissues.

The disclosed biomedical materials may be utilized in a variety of applications for interface multiple tissue regeneration/reconstruction. Suitable applications for the disclosed biomedical materials may include but are not limited to bone-periodontal ligament applications, tooth(cementum)-periodontal ligament applications, dentin-pulp complex applications, bone-mucosa applications, bone-tendon applications, bone-cartilage applications, and bone-ligament applications.

DETAILED DESCRIPTION

Figure 1:
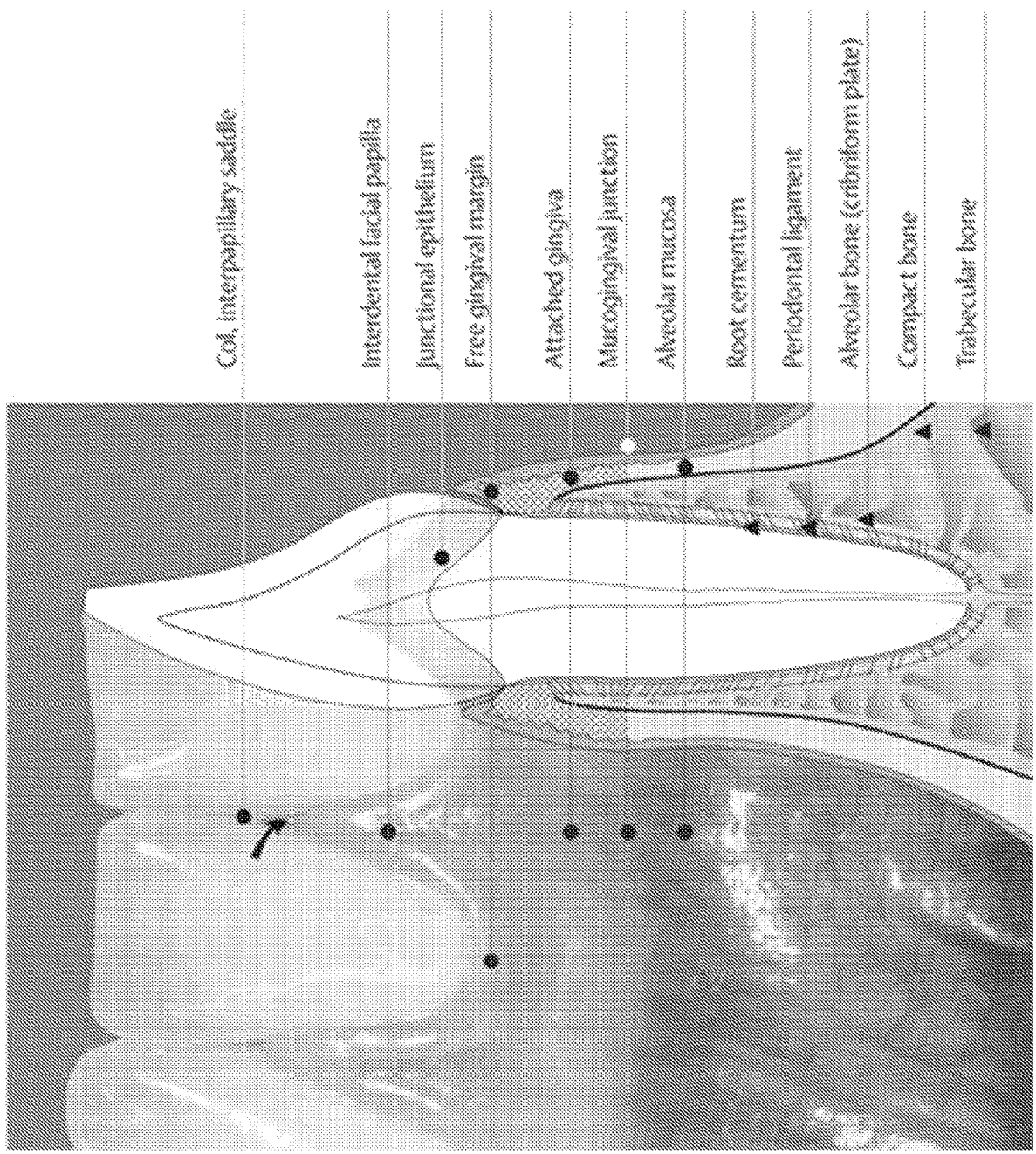
FIG. 1. Cross-sectional illustration of the structure of periodontium.

The disclosed subject matter further may be described utilizing terms as defined below.

Unless otherwise specified or indicated by context, the terms "a", "an", and "the" mean "one or more." For example, "a phase" and "layer" should be interpreted to mean "one or more phases" and "one or more layers," respectively.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, the term "phase" means a discrete component of a multi-component material. A phase may refer to a "part" and in particular the part may be a "layer." In some description of the constructs disclosed herein, the terms "phase," "part," and "layer" may be used interchangeably.

As used herein, the term "construct" may refer to a heterophasic composition or material which is a composition or material comprising two or more different phases. The term "construct" may be used interchangeable with the terms "composition" or "material." The disclosed constructs, compositions, and material may be utilized in particular to prepare biomaterials. As such, in some description of the constructs, compositions, and material disclosed herein, the term "biomaterial" specifically may be used interchangeably with the terms "construct," "composition," or "material" in general.

Description of the Disclosed Subject Matter

The disclosed subject matter relates to constructs, compositions, or material that may be used to promote soft/hard tissue regeneration and/or healing, or that may be used for sealing and/or filling bone and tooth cavities. The disclosed constructs typically incorporate a hydroxylated aromatic compound such as dihydroxybenzene (DHB) in various forms (e.g. DHB moieties incorporated in salt form, particulate form, incorporated via in-situ polymerization, incorporated via photo-polymerization, incorporated via functionalization onto polymer chains of the material, or incorporated via surface modification of the material). The disclosed constructs may be used to prepare bioactive medical/dental biomaterials that have the capability to adhere to soft/hard tissues, to form an effective seal against unwanted agents and to have antibacterial properties. Medical/dental biomaterials prepared from the disclosed constructs are capable of regenerating and/or healing more than one type of tissue. Further, medical/dental biomaterials prepared from the disclosed constructs may act as a barrier/sealant to prohibit or control infiltration of unwanted agents (e.g., water, cells, bacteria) into healing tissue.

The disclosed constructs typically are heterophasic (e.g., multi-part or multi-layered) and comprise two or more phases (or parts or layers) as described herein. One phase/part of the disclosed constructs is called the "supportive/binder phase or part," which, for example, comprises or is formed from 3D-printed polymeric materials, injectable gels, and/or collagen solutions, and which can be suturable, implantable, curable, and/or injectable. The supportive/binder phase or part typically is capable of accommodating therapeutic or bioactive molecules (e.g., antibacterial agents, therapeutic drugs, and/or growth factors) via immobilization, conjugation, and/or encapsulation.

Another phase/part of some embodiments of the disclosed constructs is called the "biomaterial matrix/compartment part," which, for example, comprises or is formed from freeze-dried collagen sponge material, polymeric particle material, (bio)ceramic granule material, dental/bone cement powder material, and/or decellularized tissue material. The biomaterial matrix/compartment part may accommodate materials such as cells and/or other bioactive agents.

The disclosed constructs optionally may include additional phases/parts for additional functionalities. The optional other phases/parts may include biomaterials such that the optional other phases/parts function as secondary barriers, provide for bioadhesion, and/or have an antibacterial effect.

Medical/dental biomaterials formed from the disclosed constructs are capable of regenerating/healing more than one type of tissue, which make them unique for multi-tissue regeneration and interface tissue engineering.

The various parts/phases of the disclosed heterophasic constructs can be suturable, implantable, curable, and/or injectable and capable of accommodating cells, therapeutic and/or bioactive molecules.

In some embodiments of the disclosed biomedical constructs, different phases/parts of the constructs may be adhered together using bioadhesives, mucoadhesives, or glues which may include but are not limited to curable resins, cyanoacrylate-based adhesives, urethane-based adhesives, polyethylene glycol derivatives, magnesium phosphate cement, ethylene glycol-oligolactide-bismethacrylate, bis(dilactoyl)-methacrylate, fibrin glue, poly(methyl methacrylate)-based resins and cements, lactide-methacrylate based systems, zinc poly carboxylate, glass ionomer cements, bisphenol-α-glycidyl methacrylate (bis-GMA) and triethyleneglycol dimethacrylate (TEGDMA), dental adhesive systems, calcium and magnesium phosphate based cements, biologically derived and/or inspired adhesives, protein-aldehyde systems, mussel adhesive proteins and mimetic polymers, collagen based adhesives, gelatin based adhesives, polymeric hydrogels, dendrimers, polyphenolic adhesives, polysaccharide based systems, and combinations thereof which optionally may be modified with to include DHB moieties. DHB moieties may be incorporated into the adhesives through chemical modification of the adhesive moieties. In some embodiments, the adhesives comprise polymers, and monomers in the backbone of the polymers are modified. Optionally, the adhesives may be blended with other polymers comprising DHB moieties, or the adhesives may be blended with nano/microparticles comprising DHB moieties deposited or coated on the surfaced of the nano/microparticles.

One characteristic of the disclosed constructs is that the various heterophases may be integrated and may comprise compounds that include DHB moieties (i.e., 1,2-dihydroxybenzene) in various forms to facilitate integration of the heterophases and/or to facilitate integration of therapeutic agents into the heterophases and/or to facilitate bioadhesion of the construct to soft/hard tissues. More specifically, the supportive/binder phase may incorporate compounds having DHB moieties or other adhesive functional chemical groups to not only provide bioadhesion to the adjacent part/tissue(s), but also to provide a platform to conjugate therapeutic and bioactive components, and also improve the bioactivity (e.g., osteoconductivity, osseointegration) of the constructs.

In some embodiments of the multi-layered constructs as contemplated herein, the multilayered constructs are adapted for use as dental-medical constructs. The various phases/layers of the dental-medical constructs may be locally functionalized with DHB moieties (e.g., at selected discrete areas) through various methods including but not limited to photo-polymerization (e.g., Ultra Violet (UV)-polymerization), in-situ polymerization, particle incorporation and surface adsorption (e.g., via coating).

In some embodiments, the disclosed subject matter may provide materials for performing methods selected from bone/endodontic sealing and/or filling, facilitating bone regeneration, performing root canal therapy, apexification treatment, pulp capping, pulpotomy, root perforation, and/or revascularization.

In some embodiments, the disclosed materials may be utilized in methods for performing bone/endodontic filling and/or sealing. In these embodiments, the disclosed materials may comprise: (1) a liquid phase as a binder phase which can be acidic, neutralized or a basic solution comprising macromonomers and/or polymers; (2) a powder mixture as a matrix phase, which may comprise calcium and/or derivative thereof (e.g., salts such as calcium oxide, calcium silicate, calcium phosphate, calcium aluminate), and/or other compounds (e.g. polymers, salts, drugs); and optionally (3) a possible third phase comprising or formed from a spongy form.

In some embodiments, the disclosed materials may be utilized as filling and/or sealing dental materials and may be applied to a wet environment of the oral cavity and offer an acceptable setting in the presence of moisture and blood. Features of the disclosed materials may provide better wetting, penetration, filling and/or sealing than prior art materials. Therefore, the disclosed materials may exhibit ease of administration in the moist environment of the mouth or bone. This is particularly important when the material is employed for root-end filling where bleeding is often difficult to control. More specifically, the disclosed materials may be utilized as bone/endodontic materials that are capable of providing improved bioactivity, induced mineralization, and bioadhesion to the target soft/hard tissues. The disclosed medical/dental materials may provide improved handling, which facilitates clinical administration, even in target sites with complicated surgical access.

The various phases/parts of the disclosed heterophasic constructs may be integrated together by the use of hydroxylated aromatic compounds, such as compounds comprising DHB moieties (e.g., 1,2-dihydroxybenzene) which can be incorporated to the different phases/parts. Firm adhesion between various phase/parts is a major drawback of hybrid biomedical constructs currently available in the market.

The presently disclosed constructs may utilize DHB moieties in various forms, such DHB moieties incorporated in particulate form, DHB moieties incorporated via in-situ polymerization, DHB moieties incorporated via photo-polymerization, DHB moieties incorporated via functionalization onto polymer chains of the material, or DHB moieties incorporated via surface modification of the material. By using DHB moieties as such, the disclosed constructs may be utilized to prepare integrated multiphasic bioactive medical/dental biomaterials having the capability to adhere to soft/hard tissues, to form an effective seal against unwanted agents and to have antibacterial properties.

Medical/dental biomaterials formed from constructs that incorporate DHB moieties not only provide attachment to the adjacent part/tissues, but also provide a platform to conjugate therapeutic and bioactive components, and also improve the bioactivity (e.g. osteoconductivity, osseointegration) of the biomaterials.

Medical and Dental Integrated Multiphasic Biomaterials for Single or Multi-Tissue Reconstruction/Regeneration The presently disclosed subject matter is related to the field of dental and medical regeneration or reconstruction and wound healing. More specifically, the presently disclosed subject matter is related to a biomedical construct for single/multi-tissue regeneration, dental/bone filling materials and/or cell expansion via modified particles.

In some embodiments, the disclosed subject matter encompasses a biomedical thin/thick construct for interface tissue engineering and guided tissue regeneration, where one or more tissues are regenerated or healed.

This disclosed subject matter also relates to designs and applications of integrated multiphasic constructs/biomaterials for single or multiple tissue reconstruction, regeneration or healing. In particular, the disclosed subject matter provides methods of producing constructs/biomaterials for use in vivo and/or clinical applications and wound healing.

Also disclosed herein are methods for designing and producing multilayered constructs/biomaterial as wound dressing. Thus, the various layers of the multilayered constructs/biomaterial can be made of resorbable or nonresorbable materials in different physical forms including and not limited to foam, hydrogel, woven or non-woven fabric, electrospun mat, and 3D printed materials. The optional outer layers may comprise (e.g. via immobilization or conjugation) antimicrobial drugs and/or peptides in order to eliminate risk of infection.

The disclosed subject matter also relates to multilayer/ multiphasic constructs/biomaterials with attachment/adhesion between phases/parts.

In some embodiments, the disclosed constructs or biomaterials may be adhesive to the target tissues including but not limited to tooth, oral mucosa, bone, and skin.

The disclosed constructs may comprise or consist of a support/binder part (e.g., as a phase or layer), which may not only provide possibly mechanical strength to the construct, but also may provide the capability of selectively localizing bioactive components present in the construct (e.g., on the side of interest which is adjacent to living tissue).

This disclosed subject matter also provides designs and methods of manufacturing constructs/biomaterials with the possibility of incorporating customized zonal organic/inorganic materials, selected porosity, selected mechanical properties, self-supporting characteristics, and localization of desired bioactive agents and cells in a phase/part of interest of the construct.

In certain embodiments, the disclosed subject matter encompasses a hybrid multiphasic construct for single or multi-tissue regeneration or healing, which comprises or consists of the following phases/parts: (1) a scaffold which acts as a supportive phase (e.g. comprising and/or formed from 3D-printed scaffolds, porous titanium construct scaffolds, and/or bioceramic scaffolds) which is capable of accommodating (e.g. via immobilization, conjugation, and/or encapsulation) therapeutic or bioactive molecules (e.g., antibacterial agents, therapeutic drugs, growth factors); (2) a biomaterial matrix (e.g., comprising or formed from a freeze-dried collagen sponge material, decellularized bone granule material, and/or a hydrogel material such as collagen material) which may adhered to the supportive phase and/or may be embedded in the supportive phase and which may accommodate cells or other bioactive agents; (3) optionally, a barrier to prohibit or control infiltration of unwanted agents (e.g. water, cells, and microorganisms) and/or to provide a platform for regeneration of a different desired tissue.

In certain embodiments, the scaffolds materials (support phase) of the disclosed constructs may be selected from metallic materials (e.g., titanium or alloys thereof), polymeric material (e.g., polylactic acid (PLA) or poly(D-lactic acid)(PDLA), polycaprolactone (PCL), polyether ether ketone (PEEK)), ceramic material (e.g., calcium phosphate, calcium silicate, zirconium oxide) or mixtures thereof. Hydroxylated aromatic moieties (e.g., DHB moieties) may be incorporated into the support phase in various methods including but not limited to surface adsorption, particle incorporation or polymer grafting.

In one aspect, the disclosed subject matter provides a method of modifying a support layer of a biomedical construct (e.g., via additional of reagents comprising hydroxylated aromatic moieties such as DHB moieties), which support layer can be suturable and adherent to an adjacent layer of the biomedical construct, thereby providing a platform to conjugate/immobilize bioactive agents (e.g., drugs, growth factors, proteins, peptides) to the support layer.

One or more phases/parts of the disclosed constructs may comprise adhesive or conjugable chemical groups including but not limited to hydroxylated aromatic moieties, such as DHB moieties and corresponding derivatives, in order to provide adhesion and/or conjugation between phases/parts and localization of bioactive agents.

The various layers in the multilayered construct may be arranged as a gradient, for example based on mechanical properties (e.g. based on elastic modulus). In some embodiments of the multi-layered constructs as contemplated herein, the various layers may comprise the same polymer but the various layers may have different glass transition temperatures and may be fused together through various adhesion methods including but not limited to thermal annealing, gluing, and use of chemicals comprising DHB moieties or derivatives.

In some applications of the disclosed materials, when the materials are used for performing bone/endodontic filling or sealing, the materials may stimulate calcification and growth of connective tissue into the root canal or defected area (such as diseased dentin/pulp complex or bone defects) in a manner that is superior than prior art bone/endodontic filling or sealing techniques. In some embodiments, the disclosed compounds/biomaterials provide bioadhesion to adjacent soft/hard tissues (e.g., pulp/dentin).

The presently disclosed subject matter can be employed in pulpotomy and partial pulpectomy procedures. In these procedures, the total or partial vital pulp is preserved and the disclosed biomedical material is applied over the vital pulp to encourage dentin/pulp bridging within the canal.

The disclosed constructs may include a powder phase, which may comprise and/or may be formed from powder mixtures, such as powder mixtures used as dental/bone filling materials. The powder mixtures may comprise additives, compounds or bioactive agents used in dental materials, treatment of bone defects, filling and/or sealing tooth cavities and root canals. Such materials and methods typically have desirable characteristics such as biocompatibility, the ability to stimulate of regeneration and regrowth of soft/hard tissue formation, antibacterial activity (e.g. $AgNO_3$), and the ability to seal tissue against unwanted microorganisms and/or their by-products in a wet environment. A powder phase of the disclosed constructs may comprise a radiopaque substance (e.g., an oxide or halogen salt of a heavy metal). In particular, the radiopaque substance may comprise $ZrO_2$, BaO, bismuth oxide, and/or bismuth trioxide. The radiopaque substance may be present at a suitable concentration, optionally from about 5 to 25% of the weight of the powder phase of the composite material.

The disclosed constructs may include a binder phase, which may comprise and/or may be formed from a liquid, such as liquids used as dental/bone filling materials. The liquid may comprise water (e.g. distilled or deionized water), water-base solutions, saline solution (e.g., normal or phosphate buffer), buffer(s), simulated body fluid solutions, and blood and blood derivatives. The pH of the liquid phase can vary from acidic to neutral to basic. The liquid may comprise other additives including but not limited to salts, drugs, silicate salts, colloidal particles (e.g. nanosilver, nanosilicate, nanotitanium oxide, nanoiron oxide) which may be present at a suitable concentration (e.g., about 0.5-25 percent by weight of the liquid).

In some embodiments, the construct for sealing and/or filling the root canal may comprise cement (e.g., mineral trioxide aggregate cement (MTA), bioceramic cement, glass ionomer cement, composite cement) optionally into which DHB moieties have been incorporated. In some embodiments, the properties of glass ionomer cement or restorative glass ionomer (in terms of mechanical strength and bonding) may be enhanced through incorporation of L-3,4-dihydroxyphenylalanine or 3,4-dihydroxyphenethylamine particles and/or functionalization of carboxylic acid components (e.g., polyacylic acid, polymethacrylic acid, ethanoic acid) with DHB moieties. Modified polymers with DHB moieties (e.g. DHB-modified alginate, or DHB-modified hyaluronic acid) also can be incorporated into various components of the glass ionomer cement.

In some embodiments, one or more phases/parts of the construct may comprise photo-curable polymers (e.g., methacrylated gelatin (GeMA), methacrylated alginate (AgMA), methacrylated chitosan, methacrylated hyaluronan).

Components of the phases/parts of the construct (e.g., layers of the construct) may be commercially available components and/or may be components that are treated with DHB moieties and incorporated with bioactive components (e.g., commercial available membranes, scaffolds, dental implants, mineral trioxide aggregate cement (MTA), bioceramic cement, glass ionomer cement, composite cement into which DHB moieties are incorporated).

The various phases/parts of the construct may be arranged to provide a gradient in microstructure of the construct (e.g., a gradient in regard to porosity or pore size). In some embodiments, one or more of the components of the constructs may act as viscosity enhancing substance to improve handling properties of the constructs.

In some embodiments, the constructs may be utilized as medical/dental materials that stimulate the body to heal.

The disclosed constructs utilize and/or comprise hydroxylated aromatic compounds such as DHB and DHB derivatives. Hydroxylated aromatic compounds and/or DHB derivatives may include but are not limited to serotonin or 5-hydroxytryptamine, norepinephrine, epigallocatechin gallate, 3,4-dihydroxyphenylalanine, 3,4-dihydroxy-L-phenylalaninenorepinephrine, 3,4-dihydroxyphenethylamine, resorcinol derivatives, hydroquinone derivatives, corresponding polymers, derivatives, copolymers and combinations thereof.

The disclosed constructs may function as multiphasic templates or scaffolds for tissue regeneration. A major challenge in fabricating multiphasic templates or scaffolds is obtaining adhesion between the various parts of the templates or scaffolds which comprise different materials. In the disclosed biomaterials, by incorporating chemical moieties (e.g., hydroxylated aromatic moieties, such as DHB moieties), or other adhesive or conjugable chemicals into the different phases, attachment between different phases is achieved. Accordingly, multi-layer constructs are contemplated herein, each layer of a multi-layer construct may comprise any composition of organic materials and/or inorganic materials. Thus one or more phase/part may be made of inorganic phase (e.g. ceramic, metal, cement) adhered to other part(s) that may be made of an organic phase.

One or more parts of the disclosed constructs may comprise biologically derived matrices (e.g. decellularized tissue). The matrices comprising decellularized tissue typically preserve the extracellular matrix (ECM) which is capable of recellularization. The ECM may comprise and/or may be formed from a hydrogel form of solubilized ECM derived from decellularized tissues of various mammalian sources (e.g. pig, cow, monkey, or human) including but not limited to cartilage, bone, dermis, pericardium, small intestinal submucosa, and urinary bladder. The matrices comprising decellularized tissue can be incorporated with various components including but not limited to growth factors, interferons, interleukins, chemokines, monokines, hormones, angiogenic factors, drugs and antibiotics, immune modulating agents (e.g., cytokines, IL2R antagonist, glucocorticoids, leucotriene antagonists), and coagulation factors (e.g., aspirin, heparin, heparin-binding proteins,). Various sterilization and crosslinking procedures can be applied to the matrices comprising decellularized tissue. The matrices comprising decellularized tissue can be used intact, solubilized or digested (e.g., partially digested) at various ranges of pH. Various ECM components of the matrices comprising decellularized tissue may include, but are not limited to elastins, collagens, laminins, glycosaminoglycans, proteoglycans, antimicrobials, chemoattractants, cytokines, and growth factors. The ECM and matrices comprising decellularized tissue can be treated in various procedures before or after decellularization including but not limited to freeze-drying (i.e., lyophilization), enzymatic digestion, air-drying, cutting, tearing, grinding, shearing, freezing, pulverize, comminuting and milling. Cells can be mixed into a neutralized solubilized gel prepared from matrices comprising decellularized tissue and/or cells may be seeded onto a neutralized solubilized gel prepared from matrices comprising decellularized tissue. The disclosed constructs may be utilized as biomaterials, which may be incubated in a suitable medium, bioreactor or incubator for a predetermined time to achieve desired features for clinical and/or in vivo implantation (e.g., cell growth on the biomaterials prior to implantation).

In a multi-layered construct as contemplated herein, a suturable support layer of the construct may be porous or dense and/or may comprise hybrid multiphasic resorbable and/or nonresorbable materials. In some embodiments, the support phase/part may comprise a resorbable material including and not limited to elastomeric polymers, biodegradable polyurethane polymers, plasticized polymers or plasticized highly ceramic (e.g., hydroxyapatite, tricalcium-phosphate, bioactive glass, and the like), optionally modified with chemical moieties such as DHB or DHB derivatives.

The disclosed constructs may comprise one or more phases or parts that comprise and/or that are formed from metals including and not limited to titanium, alloys thereof, which optionally are modified with chemical moieties (e.g., DHB and/or DHB derivatives or other conjugable and/or adhesive chemical moieties). The disclosed constructs may comprise one or more phases or parts that comprise and/or that are formed from woven and/or nonwoven fabric, mats or hollow fibers modified with chemical moieties (e.g., DHB and/or DHB derivatives or other conjugable and/or adhesive chemical moieties).

The disclosed constructs may comprise one or more phases or parts that act as a barrier/sealant to prohibit or control infiltration of unwanted agents (e.g., water, cells, bacteria) with the capability of incorporating (e.g., via immobilization and/or via conjugation) therapeutic or bioactive molecules including and not limited to drugs, peptides, proteins, antimicrobial agents, antibiofouling compounds.

The disclosed constructs may comprise one or more phases or parts that comprise a "soft" system including but not limited to gels and hydrogels. The soft system may be fabricated with various methods including but not limited to casting, molding, and additive manufacturing techniques such as 3D printing. The components of the soft system may be crosslinked physically and/or chemically.

The disclosed constructs may comprise one or more phases or parts that comprise and/or that are made of foam including and not limited to absorbent materials/polymers and highly internal phase emulsions (polyHIPEs) in particular foams that are utilized for wound dressing applications. The different phases/parts can be incorporated (e.g., via immobilization or via conjugation) with various bioactive agents including and not limited to drugs, growth factors, proteins, peptides, antimicrobial agents, antibiofouling materials.

In some embodiments, the disclosed construct may be designed for application as an implant (e.g., a construct comprising titanium, polyether ether ketone) to improve osseointegration of the construct. In applications associated with implants (e.g. in which the construct comprises metallic, polymer, or a hybrid thereof), the constructs may be designed to incorporate (e.g. via conjugation and/or via immobilization) and release bioactive agents (e.g., drugs, peptides, proteins, antimicrobial agents, and/or antibiofouling compounds). In certain embodiments the DHB moieties can be employed for surface modification of polymeric, ceramic or metallic implants (e.g. PEEK, Titanium, Zirconia) including but not limited to surface treatment and layer by layer assembly of desired (bio)polymers and/or to localize desired bioactive agents (e.g. growth factors, cytokines).

In some embodiments, the disclosed constructs may be designed and utilized as guided bone regeneration membranes. In this case, the support layer may be optimized to regenerate hard tissue, for example, where the support layer comprises osteoinductive and osteoconductive compounds (e.g. hydroxyapatite, tricalcium phosphate, bone morphogenic proteins) that optionally are modified with DHB and/or DHB derivatives. The matrix porous layer may comprise collagen or other biomaterials that may be covered by an optional barrier layer to prohibit infiltration of fibroblasts into the matrix porous layer.

Different layers/parts of the construct can be fabricated by various methods including but not limited to additive manufacturing techniques, electrospinning, phase separation, thermal sintering, layer by layer assembly, microsphere sintering, porogen leaching, gas foaming, freeze-drying and combinations thereof.

Various materials can be used preparing constructs as disclosed herein. The following materials are exemplary and may be used alone or in combination with others.

Natural polymers include and are not limited to proteins and poly(amino acids), collagen, gelatin, natural poly(amino acids), synthetic poly(amino acids), polypeptides, elastin, elastin-like peptides, albumin, fibrin, polysaccharides, polysaccharides of human origin, polysaccharides of non-human origin (e.g. chitosan, chondroitin sulfate, hyaluronic acid, alginate, carageenan, dextran). Different ceramics can be used purely or in the form of a composite and may include, but are not limited to hydroxyapatite, tricalcium phosphate, calcium phosphate salts, bioactive glasses, metals including and not limited to magnesium, iron, and titanium. Hydrogels include and are not limited to gelatin, collagen, alginate, elastin, hyaluronic acid, chitosan, and chondroitin sulfate.

Synthetic polymers include and are not limited to: poly (α-esters), polyglycolide, polylactides, poly(lactide-co-glycolide), polydioxanone, polycaprolactone, poly(trimethylene carbonate), bacterial polyesters, poly(α-esters), poly (ester amide), poly(ortho esters), polyanhydrides, polyurethanes, poly(anhydride-co-imide), cross-linked polyanhydrides, poly(propylene fumarate), pseudo poly (amino acid), poly(alkyl cyanoacrylates), polyphosphazenes, polyphosphoesters, poly(ethylene terephthalate), poly (carbonate), poly(styrene), poly(dimethylsiloxane), poly (ether ether ketone), cellulose acetate, poly (tetrafluoroethylene) and corresponding copolymers and blends thereof modified with DHB and/or DHB derivatives. One or more part/layer in the constructs can be made of bottle brush polymers and solvent-free dry polymer gels with tunable stiffness/elastic modulus to accommodate different cells.

Growth factors may include but are not limited to adrenomedullin, angiopoietin, autocrine motility factor, bone morphogenetic proteins, ciliary neurotrophic factor family, ciliary neurotrophic factor, leukemia inhibitory factor, colony-stimulating factors, macrophage colony-stimulating factor, granulocyte colony-stimulating factor, granulocyte macrophage colony-stimulating factor, epidermal growth factor, ephrins, ephrin A1, ephrin A2, ephrin A3, ephrin A4, ephrin A5, ephrin B1, ephrin B2, ephrin B3, erythropoietin, fibroblast growth factor, foetal bovine somatotrophin, GDNF family of ligands, glial cell line-derived, neurotrophic factor, neurturin, persephin, artemin, growth differentiation factor-9, hepatocyte growth factor, hepatoma-derived growth factor, insulin, insulin-like growth factors, insulin-like growth factor-1 (IGF-1), IGF-2, interleukins, IL-1, IL-2, IL-3, IL-4, IL-5, IL-6, IL-7, Keratinocyte growth factor, migration-stimulating factor, macrophage-stimulating protein, also known as hepatocyte growth factor-like protein, myostatin (GDF-8), neuregulins, neuregulin 1, neuregulin 2, neuregulin 3, neuregulin 4, neurotrophins, Brain-derived neurotrophic factor, Nerve growth factor, Neurotrophin-3, neurotrophin-4, Placental growth factor, platelet-derived growth factor, renalase, T-cell growth factor, thrombopoietin, Transforming growth factors, Transforming growth factor alpha, transforming growth factor beta, tumor necrosis factor-alpha, vascular endothelial growth factor, Wnt signaling pathway factor, and combinations thereof.

Therapeutic and/or bioactive agents (e.g. drugs, peptides, proteins, antimicrobial agents, antibiofouling compounds) optionally may be incorporated into the various phase/part(s) of the disclosed constructs via methods that include but are not limited to encapsulation, loading, conjugation and immobilization in and/or on particulate systems (e.g., microparticles, microspheres, nanoparticles, nanogels). In some embodiments, the design of the construct may be optimized to provide desired release and delivery of therapeutic and/or bioactive agents incorporated therein. In some embodiments, therapeutic and/or bioactive agents may be immobilized in the construct via the use of additional reagents (e.g., immobilizing reagents), including but not limited to heparin, lysine, corresponding polymers, and derivatives thereof. In come embodiments, additional reagents may include, but are not limited to collagen, gelatin, keratin, fibronectin, vitronectin, laminin, polypeptides, polysaccharide, derived amino acid sequence proteins, or mixtures thereof.

In the case of resorbable construct and/or components of the construct that are resorbable, the resorbable construct and/or resorbable components thereof will have a biodegradation rate as a property of the particular material. In addition, the degradability of constructs/biomaterials will further depend upon their physical properties. The thickness, porosity and crosslinking ratio of various phase/part may control the degradation rate. The degradability of each component can be controlled and optimized to match estimated growth for the particular patient, target site and application.

The microstructure, porosity, pore size and degradability of each phase/part can be adjusted and customized based on selected materials, composition, and the preparation/manufacturing process.

In some embodiments, the disclosed constructs/biomaterials may be used for treating and/or protecting spinal cord injuries. The construct may be employed to partially cover a region of interest (e.g., on or near the spinal cord).

In certain embodiments, the disclosed constructs may be utilized as microcarriers for dynamic cell expansion in vitro and/or microscaffolds for tissue regeneration, where the constructs comprise and/or consist of the following phase/parts: (1) microparticles which function as a matrix phase (e.g., polymeric particles, ceramic particle, polymer/ceramic hybrid particles, and decellularized bone granules) and which may accommodate cells or other bioactive agents; and optionally (2) a binder phase (e.g., polymeric gels, stimuli-responsive hydrogels, photo-curable macromonomers/polymers), which are capable of accommodating (e.g., via immobilization, conjugation, and/or encapsulation) therapeutic or bioactive molecules (e.g., antibacterial agents, therapeutic drugs, growth factors) agents.

In certain embodiments, when the disclosed constructs are utilized as microcarriers (MCs), the MCs can be used for dynamic cell culture to expand anchorage-dependent cells. MCs may be stirred in culture media and may yield efficient cell growth owing to a relatively large attachment surface area.

In certain embodiments, the MCs may be made of various materials including but not limited to polymers, and preferably polystyrene and copolymers thereof. The polymers can be synthesized through various polymerization methods including but not limited to chain-reaction (or addition) and step-reaction (or condensation) (e.g. radical polymerization, bulk polymerization, suspension polymerization, emulsion polymerization, microemulsion polymerization, ring-opening polymerization, atom-transfer radical-polymerization, reversible addition-fragmentation chain-transfer polymerization, or combined polymerization methods thereof). The MCs can be synthesized in situ through the above mentioned polymerization methods or combined methods thereof. The MCs can be comprising desired stimuli-responsive (e.g. temperature, light, pH, magnetic field, electric field) surface modification to provide cell detachment enzyme-free (reagent-free). The MCs may comprise DHB moieties and/or DHB derivative moieties. The MCs, in various embodiments, may be coated with DHB moieties and/or may comprise and/or may be formed from polymers comprising DHB moieties on the backbone of the polymer. The MCs may be able to provide non-specific as well as specific attachment of cells.

The MCs can be made of organic, inorganic or hybrid materials which may be used as microscaffolds to possibly form an injectable compound using a binder for tissue regeneration applications. In this approach, the MCs can be preincubated in dynamic cell culture medium to attach cells for cell therapies to be transferred to patients. In certain embodiments, the microcarriers may be dynamically cultured with (stem) cells for extended time interval to allow the stem cells to proliferate and/or to differentiate before transplantation to the site of interest.

In some embodiments, the MCs may be conjugated with therapeutic agents such as polypeptides or portions thereof which promote cell adhesion. The polypeptides may include but not limited to an amino acid sequence derived from keratin, laminin, collagen, gelatin, vitronectin, fibronectin, or mixtures thereof. Optionally, the MCs may be directly conjugated to the therapeutic agents or optionally the MCs may be indirectly conjugated via a DHB moiety linker to the therapeutic agents.

In certain embodiments, the MCs can be incorporated into collagen gels to develop an injectable system to be administered for dental socket preservation and regeneration of bone defects. Alternatively, the collagen gel can be replaced by other gel systems or composites thereof. In certain embodiments, the designed MCs can be embedded in scaffolds/biomaterials and implants designed for tissue engineering and dental/medical regeneration or reconstruction.

The disclosed materials typically exhibit desirable characteristics that may include suturability, strong adhesion between layers, and the capability of immobilizing therapeutic agents, which are advantages not provided by related prior art materials. The disclosed materials may be utilized in various applications, including but not limited to Guided Tissue Regeneration (GTR), Guided Bone Regeneration (GBR), Wound healing, Burn dressing, Surgical pads, Implant integrator, Diabetic ulcer dressing, Transdermal patches, Soft tissue dressing, Hernia meshes, as part of medical prostheses, Bed ulcer dressing, Tissue engineering scaffolds, Implants and prostheses for soft or hard tissues (if fabricated by hard materials) or at the interface of tissues (bone/periodontal ligament, tooth (cementum)/periodontal ligament, bone/mucosa, bone/tendon, bone/cartilage, and bone/ligament).

The prior art discloses various materials and methods that may be modified for use in manufacturing and applying the presently disclosed materials and methods. (See, e.g., U.S. Pat. No. 6,752,834 B2: "MEMBRANE FOR IN GUIDED TISSUE REGENERATION"; U.S. Pat. No. 5,837,278: "RESORBABLE COLLAGEN MEMBRANE FOR USE IN GUIDED TISSUE REGENERATION"; U.S. Pat. No. 6,221,109 B1: "METHOD OF PROTECTING SPINAL-AREA"; U.S. Pat. No. 6,576,015 B2: "BONE MATERIAL AND COLLAGEN COMBINATION FOR REPAIR OF INJURED JOINTS"; U.S. Pat. No. 4,587,284: "ABSORBENT POLYMER MATERIAL AND ITS PREPARATION"; U.S. Pat. No. 6,713,085 B2: "METHOD AND MEMBRANE FOR MUCOSA REGENERATION"; U.S. Pat. No. 8,460,691 B2: "Fenestrated wound repair scaffold"; U.S. Publication No. 2011/0270394 A1: "METHOD AND MEMBRANE FOR SKIN Related REGENERATION"; U.S. Publication No. 2015/0297798 A1: "EXTRACELLULAR MATRIX MESH COATING"; U.S. Publication No. 2010/0292791 A1: "FULLY SYNTHETIC IMPLANTABLE MULTI-PHASED SCAFFOLD"; and U.S. Publication No. 2006/0067969 A1: "MULTI-PHASED, BIODEGRADABLE AND OSTEOINTEGRATIVE COMPOSITE SCAFFOLD FOR BIOLOGICAL FIXATION OF MUSCULOSKELETAL SOFT TISSUE TO BONE"; the contents of which are incorporated herein by reference in their entireties.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

ILLUSTRATIVE EMBODIMENTS

The following embodiments are illustrative and should not be interpreted to limit the scope of the claimed subject matter.

Embodiment 1. A biomedical material comprising a surface for cell growth and comprising hydroxylated aromatic moieties.

Embodiment 2. The biomedical material of embodiment 1, wherein the hydroxylated aromatic moieties are dihydroxybenzene (DHB) moieties.

Embodiment 3. The biomedical material of embodiment 1 or 2, wherein the hydroxylated aromatic moieties are 1,2-DHB moieties.

Embodiment 4. The biomedical material of any of the foregoing embodiments, wherein the biomedical material is an integrated heterophasic biomedical material comprising: (1) a supportive phase; and (2) a matrix phase; wherein the supportive phase and/or the matrix phase comprise DHB moieties.

Embodiment 5. The biomedical material of embodiment 4, wherein the supportive phase comprises and/or is prepared from 3D-printed materials, titanium mesh materials, bioceramic scaffold materials, biocompatible glue materials, polymeric film materials, and/or electrospun mat materials.

Embodiment 6. The biomedical material of embodiment 5, wherein the supportive phase is, capable of holding sutures and/or has bioadhesive properties whereby the supportive phase is capable of accommodating therapeutic or bioactive molecules.

Embodiment 7. The biomedical material of any of embodiments 4-6, wherein the matrix phase comprises and/or is prepared from freeze-dried collagen sponge material, and/or decellularized tissue, whereby the matrix phase may accommodate cells and/or other bioactive agents.

Embodiment 8. The biomedical material of any of embodiments 4-7 further comprising a third phase which act as a barrier layer to prohibit or control infiltration of unwanted agents, such as water, cells, and bacteria, and the third phase comprises and/or is prepared from polycaprolactone film and/or collagen film.

Embodiment 9. The biomedical material of any of embodiments 4-8, wherein the DHB moieties are incorporated into one or more of the phases in a form or manner selected from a salt form, as part of polymerized particles, via in-situ polymerization, via photo-polymerization, via functionalization to polymer chains, and via surface modification of particles, and the DHB moieties provide adhesion between phases, improve bioactivity of the constructs and/or provide bioadhesion of the biomedical material to soft/hard tissues.

Embodiment 10. The biomedical material of any of embodiments 1-3, wherein the biomedical material is material for bone/endodontic fitting and/or sealing.

Embodiment 11. The biomedical material of embodiment 10, wherein the biomedical material comprises: (1) a liquid phase which functions as a binder phase; and (2) a powder phase which functions as a matrix.

Embodiment 12. The biomedical material of embodiment 11, wherein the liquid phase comprises macromonomers and/or polymers.

Embodiment 13. The biomedical material of embodiment 11 or 12, wherein the powder phase comprises calcium or a calcium salt such as calcium oxide, calcium silicate, calcium phosphate, and/or calcium aluminate.

Embodiment 14. The biomedical material of any of embodiments 11-13, further comprising a spongy form as a third phase, which optionally is a collagen sponge.

Embodiment 15. The biomedical material of any of embodiments 11-14, wherein the DHB moieties are incorporated in the liquid phase and/or powder phase in a form or manner selected from a salt form, as part of polymerized particles, via in-situ polymerization, via photo-polymerization, via functionalization to polymer chains, and via surface modification of particles, and the DHB moieties provide adhesion between phases, improve bioactivity of the constructs and/or provide bioadhesion of the biomedical material to soft/hard tissues.

Embodiment 16. The biomedical material of any of embodiments 1-3 wherein the biomedical material is a hybrid multiphasic construct for single or multi-tissue regeneration or healing.

Embodiment 17. The biomedical material of embodiment 16, comprising (1) a scaffold phase that acts as a supportive phase; and (2) another phase which acts as a biomaterial matrix.

Embodiment 18. The biomedical material of embodiment 17, wherein the scaffold phase comprises or is prepared from 3D-printed scaffold material, porous titanium material, bioceramic scaffold material, and the scaffold material preferably is capable of accommodating therapeutic or bioactive molecules.

Embodiment 19. The biomedical material of embodiment 17 or 18, wherein the biomaterial matrix comprises and/or is prepared from freeze-dried collagen sponge material, and/or decellularized bone granule material, optionally where the biomaterial matrix is embedded partially or throughout the supportive phase and may accommodate cells or other bioactive agents.

Embodiment 20. The biomedical material of any of embodiments 17-19, further comprising a third phase which acts as a barrier to prohibit or control infiltration of unwanted agents and/or which provides a platform for regeneration of a different desirable tissue.

Embodiment 21. The biomedical material of any of embodiments 17-20, wherein one or more of the phases of the biomedical material incorporate the DHB moieties or other chemicals.

Embodiment 22. The biomedical material of any of embodiments 1-3, wherein the biomedical material is a microcarrier for dynamic cell expansion in vitro and/or a microscaffold for tissue regeneration.

Embodiment 23. The biomedical material of embodiment 22, comprising microparticles which act as a matrix phase and which may accommodate cells or other bioactive agents.

Embodiment 24. The biomedical material of embodiment 23, wherein the microparticles comprise and/or are formed from polymeric particles, ceramic particles, polymer/ceramic hybrid particles, and/or decellularized bone granules.

Embodiment 25. The biomedical material of embodiment 23 or 24, further comprising a binder phase which comprises and/or is formed from polymeric gels, stimuli-responsive hydrogels, and/or photo-crosslinkable macromonomers/polymers, and which is capable of accommodating therapeutic and/or bioactive molecules.

Embodiment 26. The biomedical material of any of embodiments 23-25, wherein the microcarrier and/or microscaffold incorporate the DHB moieties in a form or manner selected from a salt form, polymerized particle form, via in-situ polymerization, via photo-polymerization, via functionalization of polymer chains forming the phase, and via surface modification, which the DHB moieties preferably aid in integration of the microcarrier and/or microscaffold, improve bioactivity of the microcarrier and/or microscaffolds and/or provide for bioadhesion of the microcarrier and/or microscaffold to soft/hard tissues.

EXAMPLES

The following examples are illustrative and should not be interpreted to limit the scope of the claimed subject matter.

Example 1: Construct 1: Biomedical Integrated Multilayered Constructs for Single or Multi-Tissue Regeneration or Healing In certain embodiments, the disclosed construct is a multilayered construct utilized for single or multi-tissue regeneration or healing (e.g., as a guided tissue regeneration membrane, as an interface tissue engineering construct, or as a wound dressing membrane). In this example, the disclosed construct may comprise the following phase/parts: (1) a layer that functions as a supportive part (e.g. comprising and/or prepared from 3D-printed materials, titanium mesh materials, bioceramic scaffold materials, biocompatible glue materials, polymeric film materials, and/or electrospun mat materials), which supportive part is capable of holding sutures, and/or comprising a bioadhesive capable of accommodating (e.g. via immobilization, conjugation, encapsulation) therapeutic or bioactive molecules (e.g., antibacterial agents, therapeutic drugs, growth factors); (2) a second layer as a biomaterial compartment (e.g., comprising and/or prepared from freeze-dried collagen sponge material, and/or decellularized tissue material) which biomaterial compartment may accommodate cells and/or other bioactive agents; and optionally (3) a third layer (e.g., comprising and/or prepared from polycaprolactone film, and/or collagen film) that may act as a barrier layer to prohibit or control infiltration of unwanted agents (e.g., water, cells, and/or bacteria); and (4) adhesive or conjugable moieties (e.g. DHB moieties incorporated into one or more of the layers ((1), (2), and/or (3)) in various forms (e.g., incorporated in salt form, as part of polymerized particles, via in-situ polymerization, via photo-polymerization, functionalization to the polymer chains, via surface modification of particles)). Preferably, the DHB moieties provide adhesion between the layers, improve bioactivity of the constructs, and/or provide bioadhesion to soft/hard tissues.

Figure 2:
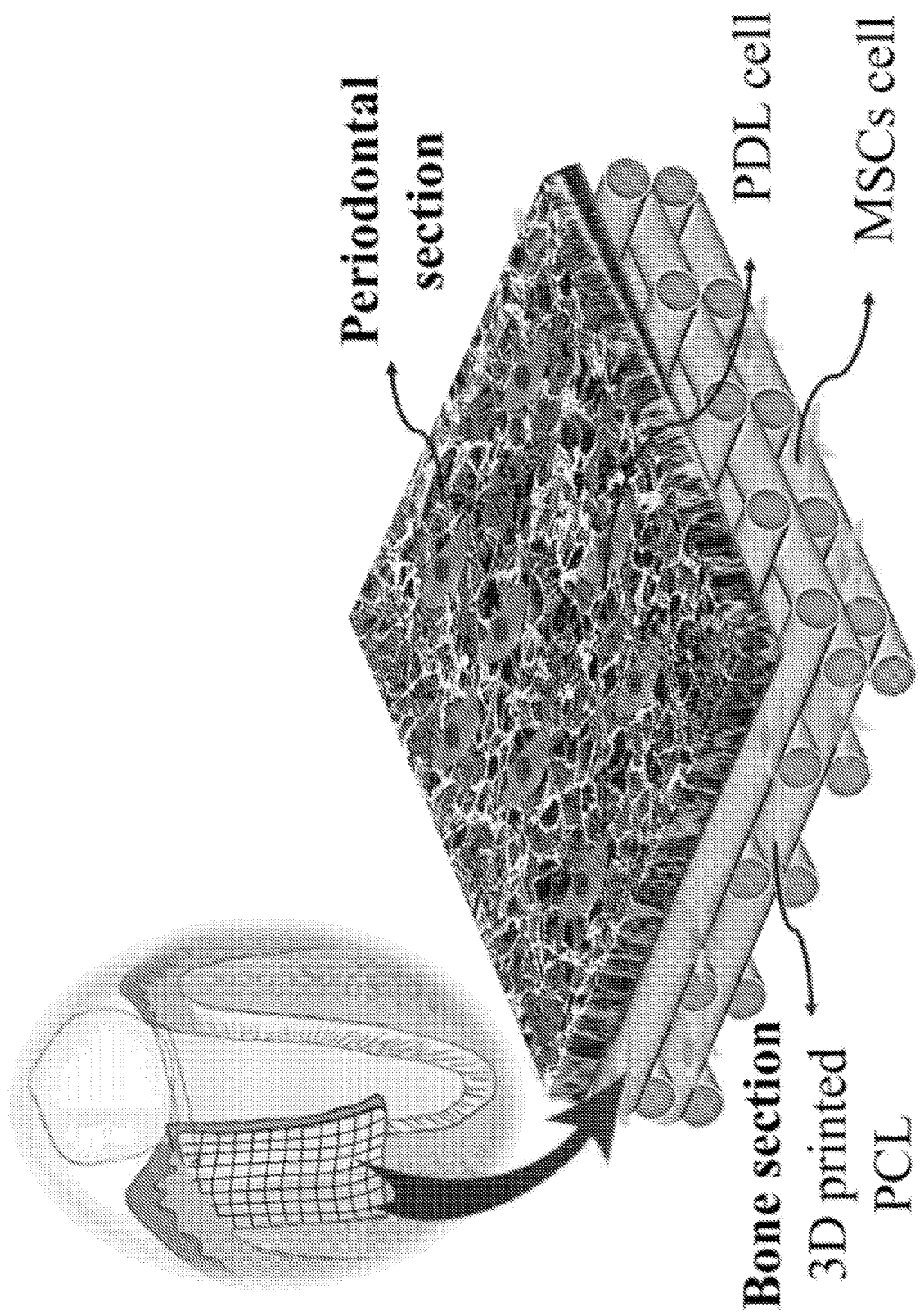
FIG. 2. Illustrative scheme of a biomedical hybrid membrane for PDL-bone multi-tissue regeneration.

The designed constructs may be applicable in guided tissue regeneration and/or interface tissue engineering. Such a construct, is particularly suitable for use in guided tissue regeneration, in particular for use in vivo in the reconstruction of bone or cartilage tissue. Guided tissue regeneration or as an example guided bone regeneration is a surgical procedure that uses barrier membranes to direct the growth of desired tissue at the sites of interest and prevent the growth of unwanted tissue. Regeneration and integration of multi-tissues on the same construct is of great interest. The developed designs for interface tissue engineering or membrane for guided tissue regeneration so far commonly suffer from poor attachment and adhesion between various sections (layers), and/or lack of controllable introduction of therapeutic or bioactive molecules to the desired site. The designed construct fulfills structural support, mechanical properties while providing firm adhesion between layers, incorporation of bioactive components (e.g., drugs, growth factors) and accommodation of different cells to achieve optimal growth environment for tissue formation. The construct may be suturable. Various parts of the biomedical suturable integrated constructs for single or multi-tissue regeneration with the capability of incorporating therapeutic agents is shown in the scheme illustrated in FIG. 2. Various layers can be included or omitted from the scheme illustrated in FIG. 2.

Example 1.1: Multilayered Membrane for Guided Tissue Regeneration

Background: The periodontal disease therapy is of great importance in the healthcare system as it significantly affects functionally and psychologically of individuals. Because of complex structure of periodontium, which is composed of soft tissue (gingiva periodontal ligament), and hard tissue (cementum, bone), the outcome of conventional treatment of periodontal disorders is unpredictable (see FIG. 1). The design of complex scaffolds capable of guided periodontal regeneration has shown to promise therapeutic outcomes. Guided tissue regeneration approaches rely on the space maintenance and selective cell repopulation of the defect. The periodontal tissue regeneration consists of the placement of a hybrid membrane over the defect to regenerate periodontium by accommodation of periodontal ligament cells, osteoblasts or their progenitors as well as delivery of desired growth factors and bioactive agents.

In this example a multilayered membrane construct is presented for guided tissue regeneration. The first layer is a supportive layer which is a mesh fabricated using 3D printing technique for hard tissue regeneration. This layer is composed of modified polycaprolactone (PCL) with functionalized DHB moieties, and comprising immobilized bone morphogenic protein (BMP-2). The second layer is a porous collagen matrix fabricated with freeze-drying method to support soft tissue regeneration.

Methods: Polycaprolactone (PCL) mesh sheets were fabricated by means of 3D printing technique. PCL mesh layer was printed by hot melt extrusion using a commercial bioprinting instrument (3D-Bioplotter® Manufacturer Series, Envisiontec GmbH, Germany). PCL granules were loaded into a steel cylinder sealed and inserted into a high temperature head of the machine with a temperature set to 130° C. The system was purged and pressurized with nitrogen stream and incubated for 10 min to be equilibrated. CAD/CAM stereolithography files were designed using the Bioplotter® software. PCL mesh construct was printed layer-by-layer with 0.5 mm distance between strands and a 90 degree shift between layers extruded from a nozzle with 0.4 mm inner diameter. The pressure and dispensing speed were 2.5 bar and 4 mm/s, respectively, and meshes of 15×15×0.2 mm$^3$ were printed.

The fabricated PCL constructs were functionalized to have better cellular attachment and also provide interfacial adhesion to the other compartment (soft tissue layer). PCL constructs were immersed in 5 wt % 2-(3,4-Dihydroxyphenyl)ethylamine, solution for 1 h at 37° C. The resulting constructs were then rinsed three times in deionized water and dried. The scaffolds treated were immersed in 10 mL deionized water pH 5.5. Hydrocaffeic acid (120 mg) in 5 mL of distilled water and ethanol (1:1 v/v) were added to the water, and incubated for 12 h. Finally, the constructs were washed with water and dried. The resultant functionalities on the surface provide attachment which offer better protein condensation and cellular attachment. The modified PCL (MPCL) mesh was covered by collagen solution (1 wt %) followed by freeze-drying to form porous matrix layer. The modified PCL (MPCL) mesh was incubated with bone morphogenic protein (BMP-2) to immobilize it.

3D Laser Measuring Microscopy (Olympus, Japan) and SEM (JEOL-JSM) were used for imaging of the constructs. The constructs were gold coated before SEM imaging. The periodontal ligament (PDL) fibroblasts and mesenchymal stem cell (MSCs) were co-cultured onto the double-layered membrane, collagen and MPCL layers, respectively. The schematic representation of the double layer membrane for guided tissue regeneration is shown in the scheme illustrated in FIG. 2.

Figure 3:
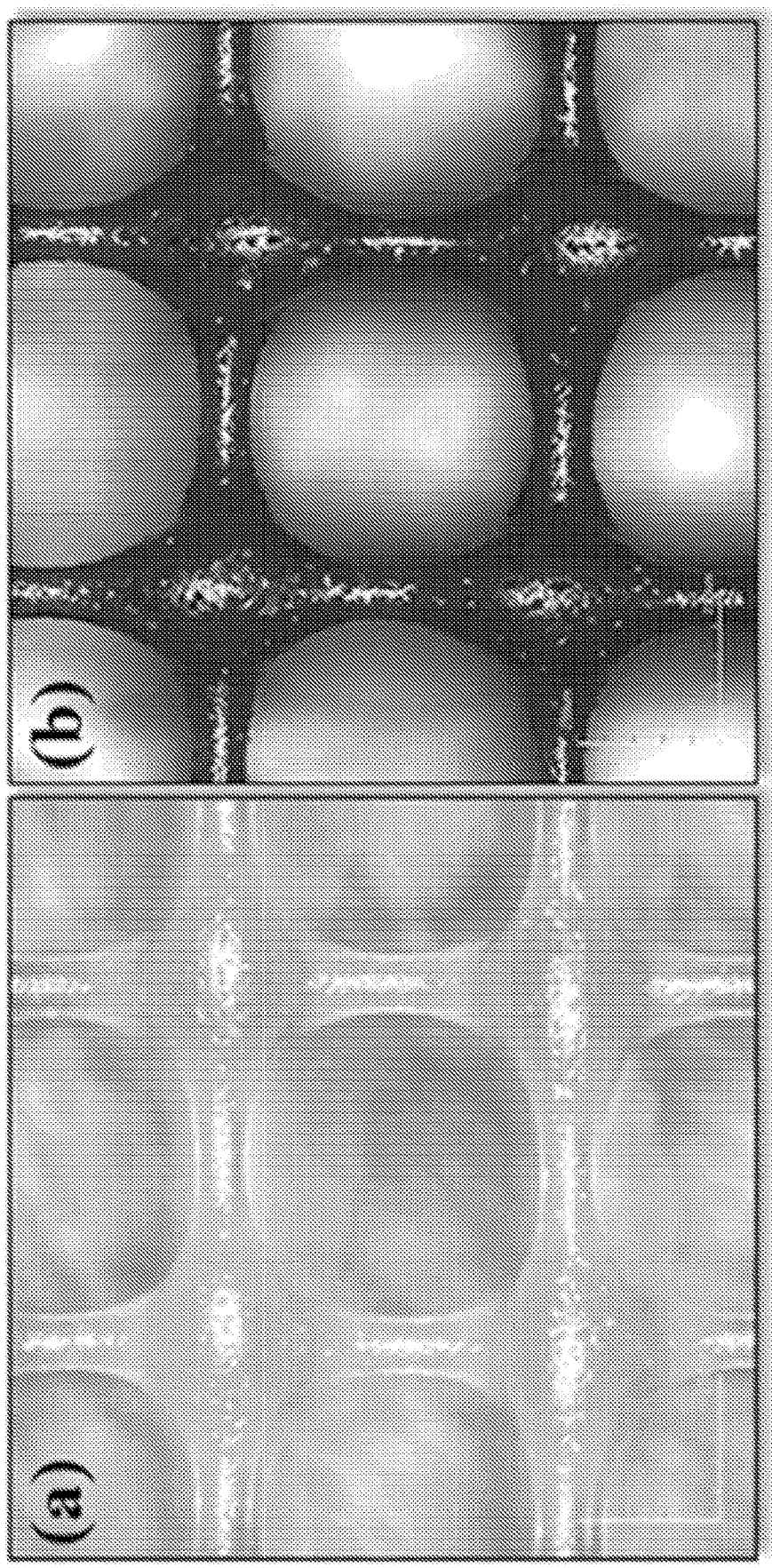
FIG. 3. Micrographs of PCL (a) and MPCL (b) 3D printed meshes as the supportive layer in the biomedical membrane constructs for multi-tissue regeneration.
Figure 4:
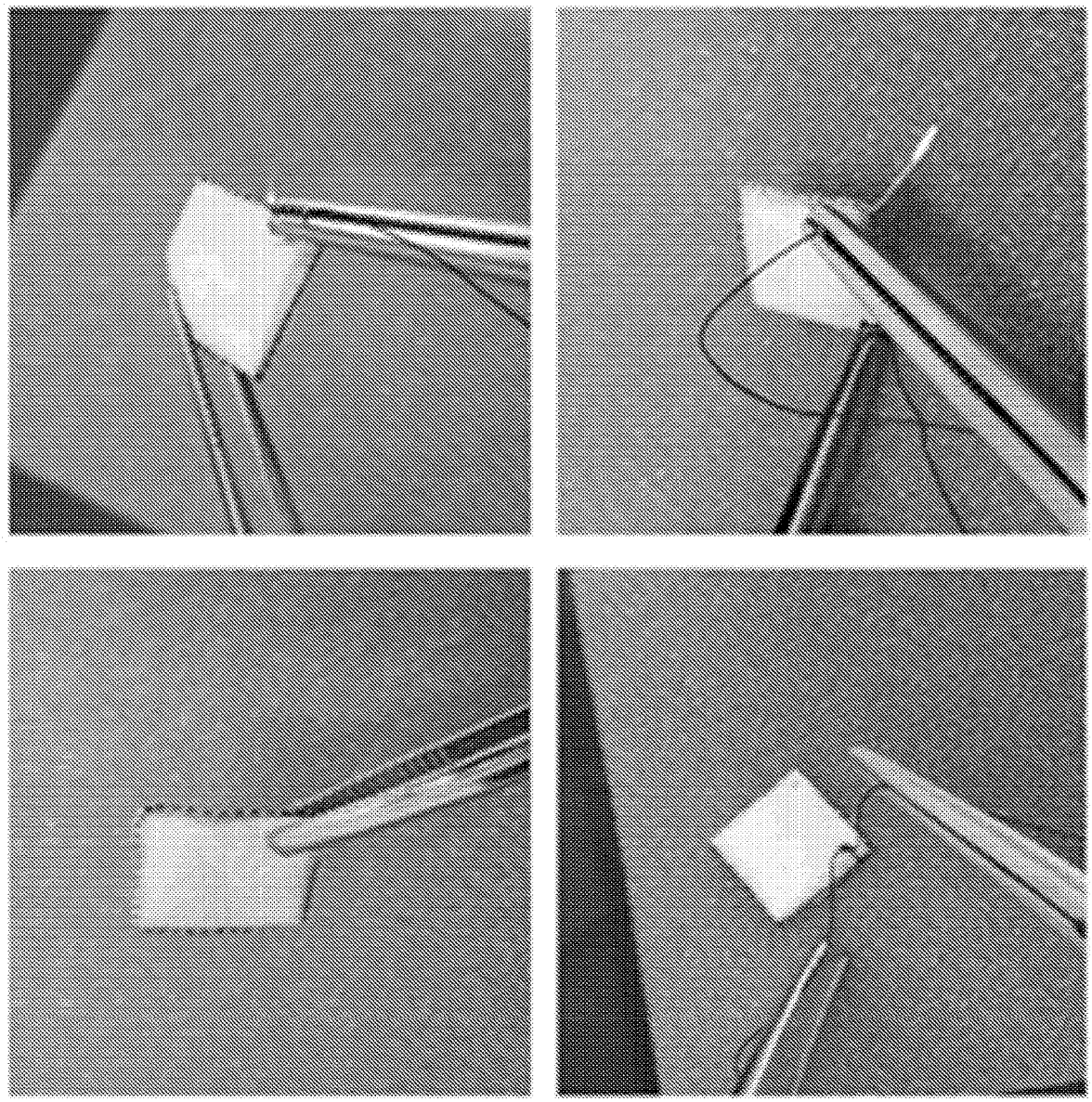
FIG. 4. Suturability of MPCL/collagen hybrid membrane for PDL-bone regeneration.
Figure 5:
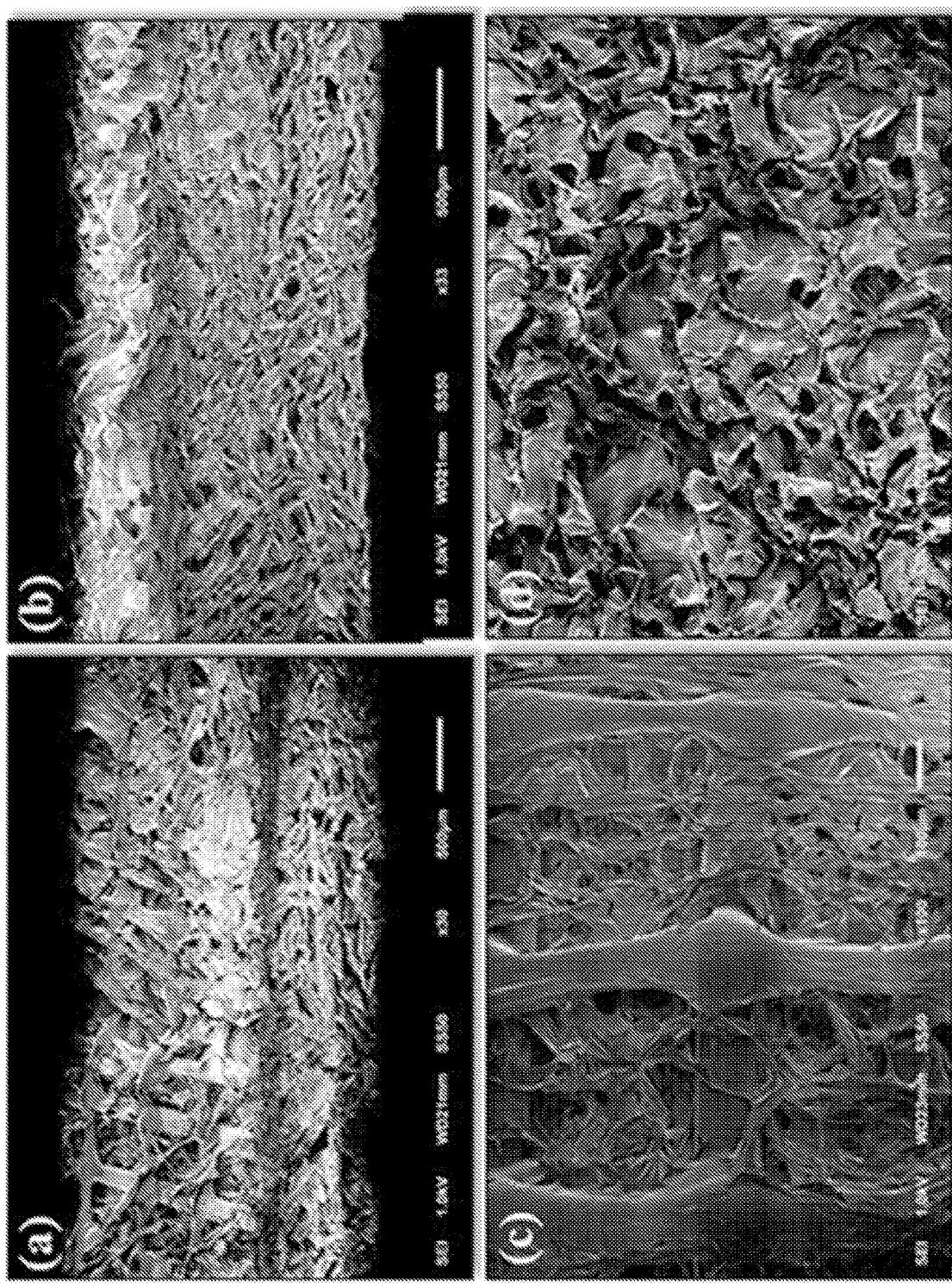
FIG. 5. Scanning Electron Microscopy of MPCL/collagen membrane constructs for multi-tissue regeneration ((a) tilted view, (b) cross section, (c) bone section, (d) periodontal section).
Figure 6:
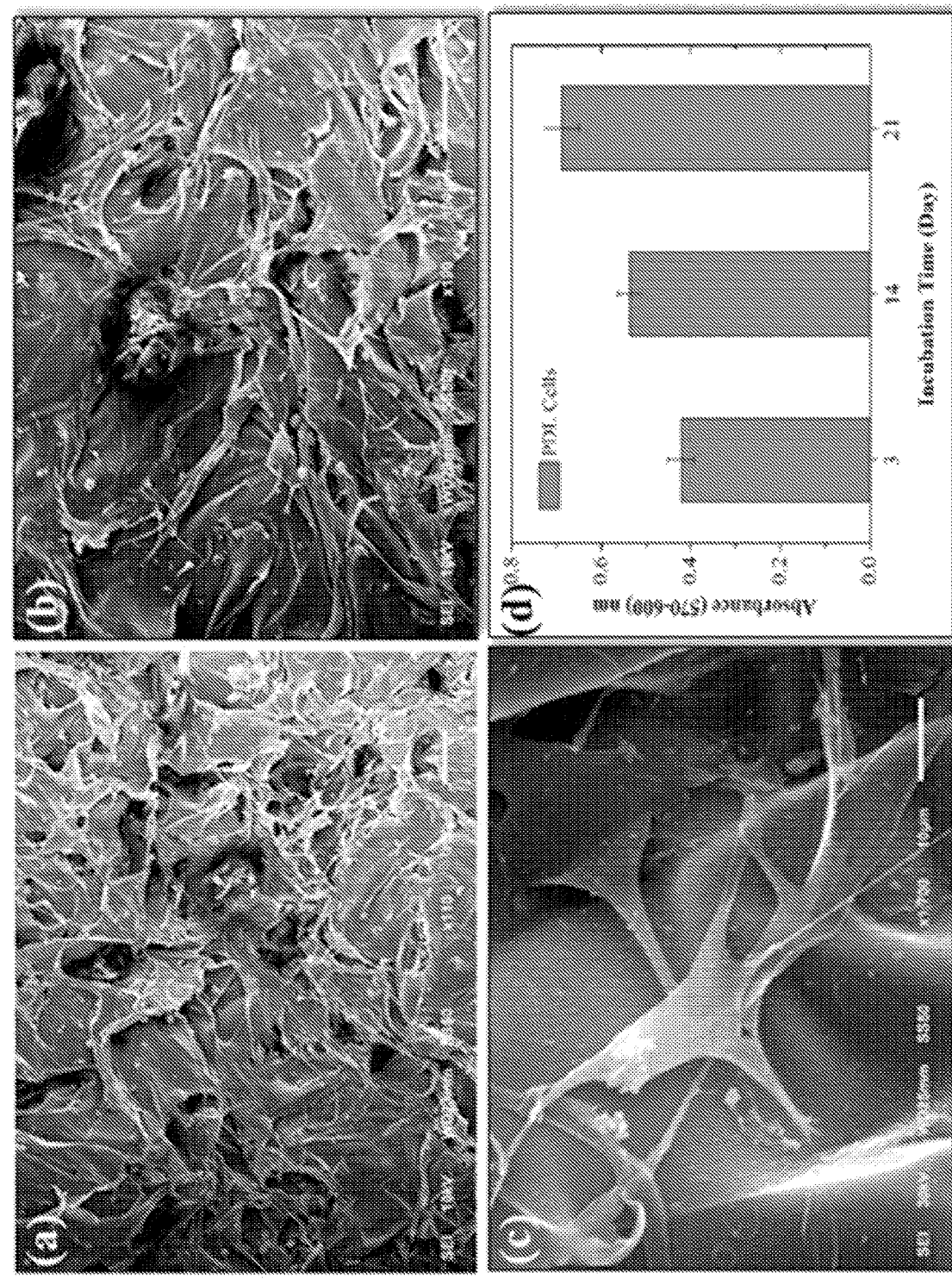
FIG. 6. (a), (b), (c) Scanning electron microscopy of PDL fibroblasts attached on the collagen layer. (d) Proliferation rate of PDL fibroblasts over 21 days analyzed by Presto Blue Assay.
Figure 7:
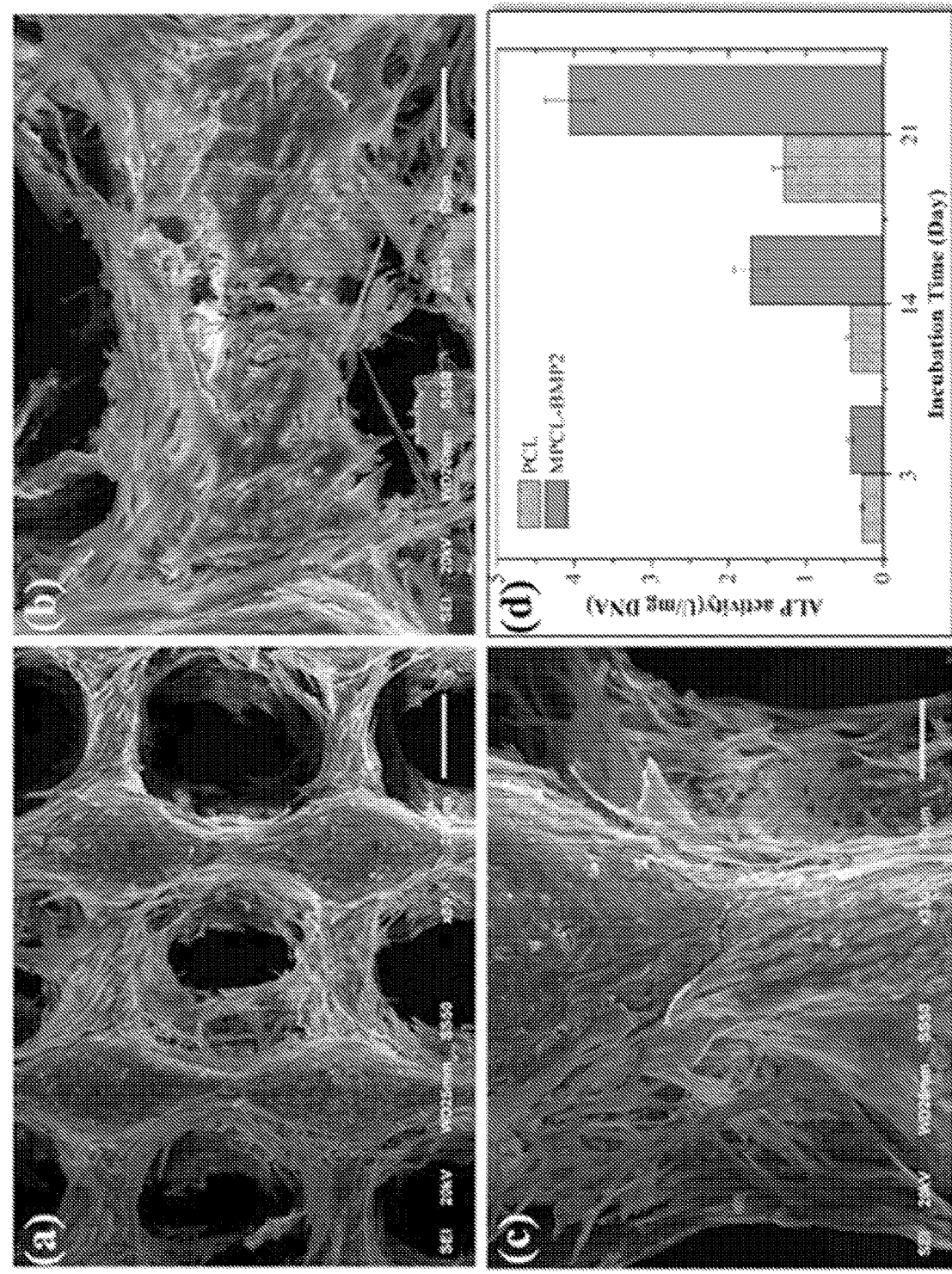
FIG. 7. (a), (b), (c) scanning electron microscopy of differentiated MSCs after 21 days attached on the MPCL 3D printed supportive layer. (d) ALP activity of MSCs cultured on PCL and MPCL-BMP2 during the 21 days analyzed by ALP assay and DNA Pico green assay.

Micrographs of 3D printed PCL and MPCL meshes as the supportive layer in the biomedical membrane constructs for multi-tissue regeneration are shown in FIG. 3. As demonstrated in FIG. 4, the disclosed double-layered membrane construct showed high suture retention strength, and requisite strength to hold suture. FIG. 5 displays scanning electron micrographs of MPCL/collagen membrane construct, which show firm adhesion between the bone and periodontal compartments. The scanning electron micrographs of PDL fibroblasts attached to the collagen layer (periodontal compartment) are shown in FIG. 6. As can be seen, the cells were well spread onto the membrane and could not infiltrate to the bone compartment, which provide guided bone-periodontal tissue regeneration. Furthermore, the collagen layer supported the proliferation of PDL fibroblasts. FIG. 7 demonstrates the effectiveness of functionalization (MPCL bone compartment) on the cell attachment and proliferation. As shown, the functionalized MPCL layer was robustly prone to accommodate MSCs and support their proliferation. The cellular assays revealed that incorporation of BMP2 onto the MPCL surface significantly improved the bioactivity and proliferation of the cells. The interfacial treatment of designed membrane improved their affinity to induce MSCs to differentiate (ALP activity) and generate their extracellular matrix. The designed constructs have the capability to support the regeneration of bone/periodontal interface.

Example 2: Construct 2: Microcarriers for Dynamic Cell Expansion In Vitro and/or Microscaffolds for Tissue Regeneration In certain embodiments of the presently disclosed materials, the material is characterized as a microcarrier for dynamic cell expansion in vitro and/or a microscaffold for tissue regeneration. The microcarrier and/or microscaffold may comprise the following phase/parts: (1) microparticles which act as a matrix phase (e.g., where the microparticles comprise and/or are formed from polymeric particles, ceramic particles, polymer/ceramic hybrid particles, and/or decellularized bone granules), and which microparticles may accommodate cells or other bioactive agents; (2) an optional binder phase (e.g., which comprises and/or is formed from polymeric gels, stimuli-responsive hydrogels, and/or photo-crosslinkable macromonomers/polymers), and which binder phase is capable of accommodating (e.g., via immobilization, conjugation, and/or encapsulation) therapeutic and/or bioactive molecules (e.g., antibacterial agents, therapeutic drugs, growth factors). Preferably, the disclosed microcarrier and/or microscaffold include DHB moieties which may be incorporated into one or more phases of the microcarrier and/or microscaffold in various forms (e.g. incorporated in salt form, polymerized particle form, via in-situ polymerization, via photo-polymerization, via functionalization of polymer chains forming the phase, via surface modification of particles), which the DHB moieties preferably aid in integration of the microcarrier and/or microscaffold, improve bioactivity of the microcarrier and/or microscaffolds and/or provide for bioadhesion of the microcarrier and/or microscaffold to soft/hard tissues.

Microcarriers (MCs) may be used in dynamic cell culture to expand anchorage-dependent cells. MCs may be stirred in culture media and in order to yield efficient cell growth owing to their large attachment surface area. In some embodiments, the MCs may comprise DHB groups. The MCs, in various embodiments, are coated with DHB groups or composed of polymers comprising DHB groups on their backbone. The MCs are able to provide non-specific as well as specific attachment of cells. The DHB groups present on the surface of MCs provide incorporation (e.g. immobilization, conjugation) of various bioactive agents (e.g. growth factors, polypeptides, polymers, etc) to provide biospecific cell adhesion and tuning the properties of the attached (stem/progenitor) cells (e.g. attachment, proliferation, differentiation). The MCs can be made of organic, inorganic or hybrid materials to be used as microscaffolds to possibly form an injectable compound using a binder for tissue regeneration applications. In this approach, the MCs can be preincubated in dynamic cell culture medium to attach cells for cell therapies to be transferred to patients. In certain embodiments, the microcarriers may be dynamically cultured with (stem) cells for extended time interval to proliferate and/or differentiate before transplantation to the site of interest. The MCs can be made of a broad range of synthetic as well as natural materials to offer a wide spectrum of features including tunable size, roughness, density, porosity, and surface chemical functionalities.

Construct 2. Microcarriers for Dynamic Cell Expansion In Vitro and/or Microscaffolds for Tissue Regeneration Example 2.1

In one example, spherical polymeric microcarriers (MCs) were generated and their surface were treated to immobilize desired biomolecules as described below to improve cell adhesion and bioactivity. The treated microparticles were then dynamically seeded with mesenchymal stem cells.

The spherical polymeric MCs were fabricated using droplet generation technique. 600 mg poly (DL-lactide) (PDLA) was first dissolved in 20 ml of dichloromethane and added dropwise to stirring aqueous polyvinyl alcohol solution (0.5 wt %) at room temperature. The resulting emulsion was gently stirred until the organic solvent was extracted from the PDLA MCs. Afterward, the microspheres were filtered and rinsed with deionized water. MCs were then separated selectively into the following size ranges by using different sieves: <75 µm; 75-150 µm; 150-300 µm; 300-425 µm; 425-500 µm.

Figure 8:
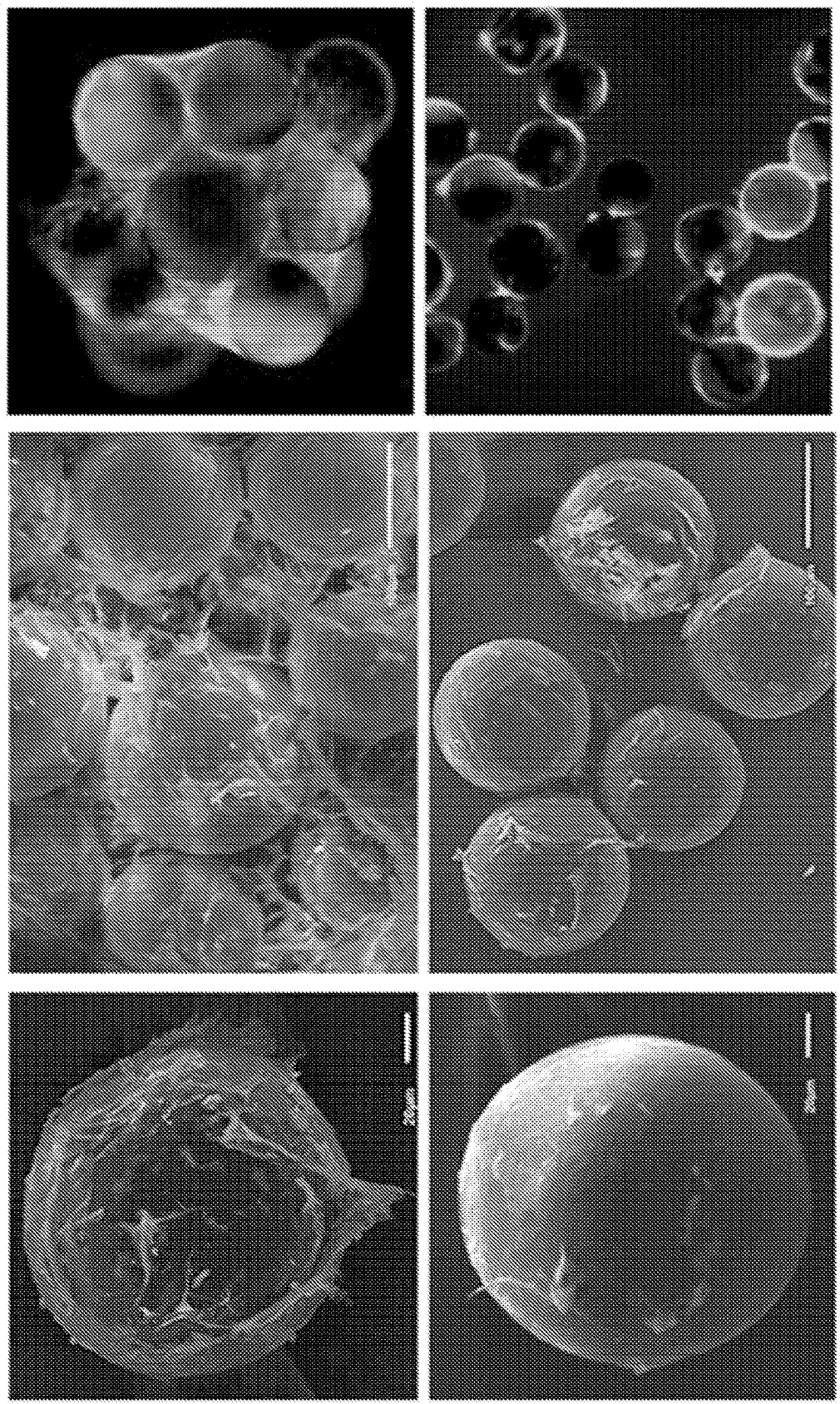
FIG. 8. Scanning electron microscopy (SEM) images and fluorescent images of modified microcarriers (upper images) and unmodified microcarriers (lower images) dynamically cultured with mesenchymal stem cells.

The following protocol was used to treat MCs and immobilize desired biomolecules in order to increase the cellular adhesion and proliferation (cell bioactivity). The MCs (100 mg) were first functionalized with DHB by soaking in alkaline 3,4-dihydroxyphenethylamine solution for 12 h at 25° C. followed by washing with distilled water. The MCs were then functionalized with fibronectin (20 mM in buffer solution), vitronectin (20 mM in buffer solution), collagen (0.1 wt %), bovine serum albumin (BSA, 0.1 wt % in buffer) for 6 h at 37° C. After rinsing the different particles several times with distilled water, the mesenchymal stem cells were dynamically cultured onto the particles using spinner flasks. FIG. 8 provides scanning electron microscopy (SEM) images and fluorescent images of modified microcarriers (upper images) and unmodified microcarriers (lower images) dynamically cultured with mesenchymal stem cells.

The in vitro cellular assays revealed that immobilization of biomolecules onto the surface significantly improves the bioactivity and proliferation of the cells. It was found that the functionalization of designed MCs with suitable biomolecules through surface DHB functionalities is critical to improve the affinity of MCs for cell adhesion, proliferation, and activity.

In certain embodiments, the biomolecules including but not limited to collagen, gelatin, keratin, fibronectin, vitronectin, laminin, polypeptides, polysaccharide, derived amino acid sequence proteins, or mixtures thereof.

In certain embodiments, the MCs can be incorporated into collagen gels to develop an injectable system to be administered for dental socket preservation and regeneration of bone defects. The collagen gel can be replaced by other gel systems or composites thereof.

In certain embodiments, the designed MCs can be embedded in scaffolds and implants designed for tissue engineering and regenerative medicine.

Example 2.2

In this example, polymeric MCs are designed for in vitro cell expansion and 3D cell culture for cellular science and drug discovery application. The designed MCs provide the capability to be dispersed in culture media and yield efficient cell growth owing to their large attachment surface area. The MCs were fabricated based on polystyrene comprising DHB moieties on their backbone. The MCs are able to provide non-specific as well as specific attachment of cells. Polystyrene comprising DHB moieties was synthesized using copolymerization of styrene and a monomer comprising DHB moieties (N-(3,4-Dihydroxyphenethyl) methacrylamide, DOPMAm). DOPMAm was synthesized using 3,4-dihydroxyphenethylamine hydrochloride and methacryloyl chloride. The 1,2-DHB groups were then chemically protected by chlorotriethylsilane. Free radical copolymerization of protected DOPMAm and styrene was performed using azobisisobutyronitrile for 12 h at 60° C. The resultant copolymer was deprotected by using tetra-n-butylammonium fluoride to obtain poly(styrene-co-DOPMAm). The spherical MCs were generated based on the synthesized poly(styrene-co-DOPMAm) using the droplet generation technique as described in Example 4.1. The in vitro cellular assays revealed that the MCs based on poly(styrene-co-DOPMAm) show superior cell adhesion and proliferation. In next step, the MCs based on poly(styrene-co-DOPMAm) were incubated with fibronectin, vitronectin, collagen, BSA as described in Example 4.1. The in vitro cellular assays revealed that immobilization of biomacromolecules onto the surface of poly(styrene-co-DOPMAm)-based MCs significantly improves the bioactivity and proliferation of the cells. It was found that the designed MCs after treatment through surface DHB functionalities provide appropriate cell adhesion, proliferation, and activity.

Example 2: Construct 3: 3D Cell Culture Dish

Microsize hemispherical particles based on poly(styrene-co-DOPMAm) was attached to the adherent/nonadherent cell culture dishes. In certain embodiments, hemispherical particles and/or culture plate are functionalized with desired biomolecules. Single or multiple types of cells can be cultured on the invented dishes for different applications including but not limited to study cellular cross-talk, drug discovery, and cancer research.

Example 3: Construct 3: Dental/Bone Filling or Sealing Materials

One aspect of the disclosed constructs relates to bone/endodontic filling and/or sealing biomaterials, comprising the following components: (1) a liquid phase as a binder phase which can be acidic, neutralized, or a basic solution comprising and/or formed from macromonomers and/or polymers; (2) a powder mixture as a matrix phase, which may comprise and/or be formed from calcium and/or calcium salt derivatives (e.g. calcium oxide, calcium silicate, calcium phosphate, calcium aluminate), and/or other compounds e.g. polymers, salts, drugs); optionally (3) a third phase that is a spongy form (e.g. a collagen sponge). Both liquid and powder phases may be incorporated with DHB moieties in various forms (e.g., incorporated in salt form, as part of polymerized particles, via in-situ polymerization, via photo-polymerization, functionalization to the polymer chains, via surface modification of particles). Preferably, the DHB moieties provide adhesion between layers, improve bioactivity of the constructs, and/or provide bioadhesion to soft/hard tissues. Owing to the nature of the compositions of the presently disclosed subject matter and incorporation of DHB moieties, the compositions stimulate calcification and growth of connective tissue into the root canal or defected area (such as diseased dentin/pulp complex or bone defects) much more efficiently than prior art materials.

The powder component may comprise other additives, compounds or bioactive agents used in dental materials, treatment of bone defects, filling and/or sealing tooth cavities and root canals. Such materials preferably have one or more characteristics selected from: biocompatibility, ability to stimulate regeneration and regrowth of soft/hard tissue, antibacterial activity (e.g. $AgNO_3$), and an ability to seal against unwanted microorganisms and/or their by-products in a wet environment. The powder phase in the construct comprises a radiopaque substance (e.g., a heavy metal and/or an oxide or halogen salt of a heavy metal). In particular, the radiopaque substance may comprise $ZrO_2$, BaO, bismuth oxide, and/or bismuth trioxide. Preferably the radiopaque substance is present in the construct or a component thereof (e.g., in the powder component of the construct) at a concentration from 5 to 25% of the weight of the construct and/or powder component of the composite material.

The liquid phase may comprise water (e.g. distilled or deionized water), water-based solutions such as saline solutions (e.g., normal, phosphate buffer), buffer(s), simulated body fluid solution, blood and blood derivatives. The pH of the liquid phase can vary from acidic to neutral, to basic. The liquid phase may include other additives including but not limited to salts, drugs, silicate salts, colloidal particles (e.g. nanosilver, nanosilicate, nanotitanium oxide, nanoiron oxide), preferably at a concentration within a percentage range of about 0.5-25 percent by weight.

In some embodiments, the construct for sealing and/or filling the root canal may comprise DHB-incorporated cement (e.g. mineral trioxide aggregate cement (MTA), bioceramic cement, glass ionomer cement, composite cement into which DHB and/or DHB moieties have been incorporated).

In some embodiments, one or more of the components of the constructs may act as a viscosity enhancing substance to improve handling properties of the constructs.

In some embodiments, the disclosed constructs adhere to adjacent soft/hard tissues (e.g. pulp/dentin) (i.e., the constructs have bioadhesive properties).

In some embodiments, the constructs may be utilized as medical/dental materials that stimulate the body to heal.

The disclosed constructs and materials may be employed in treatment procedures that include, but are not limited to, pulpoomy and partial pulpectomy procedures. In these procedures, the total or partial vital pulp is preserved and the disclosed constructs or materials are applied over the pulp to encourage dentin/pulp bridging within the canal.

Construct 3. Dental/Bone Filling or Sealing Materials

Background: In certain embodiments, the disclosed constructs and material may be utilized in methods such as bone/endodontic sealing and/or filling and methods for bone regeneration, root canal therapy and/or apexification treatment methods and/or pulp capping and/or pulpotomy and/or root perforation and/or revascularization methods.

Root canal extends from a normal tooth crown to a root to accommodate the formed pulp in the vessel. Currently, the conventional clinical procedure to treat damaged dental tissues is root canal therapy and restorative treatment, which includes cleaning and shaping of the pulp chamber and the replacement of the dentin-pulp tissue with biocompatible materials. Such procedures have several drawbacks including losing viability and biological functions of teeth and becoming subject to post-treatment failures and secondary infections.

Apexification therapy is commonly implemented to the damaged pulp tissue of a young (immature) tooth. Conventionally, the diseased pulp tissue is removed and calcium hydroxide or mineral trioxide aggregate (MTA) cement is applied to provide hard tissue formation and to close the apical part of the root canal.

The pulp tissue possesses the capability to reconstruct tissues in the root canal. Such intrinsic regenerative potential of connective tissue to proliferate into the root canal of an immature tooth is referred to as "revascularization."

In case of root perforation(s), root-end filling materials can be employed. Such materials should be able to fill the perforation site effectively and block the communication between the underlying periodontium apparatus and the oral cavity. Hence, an appropriate perforation repair material is needed in the art.

In certain dental procedures, in contrast to traditional endodontic treatment, the tooth pulp is left intact. When the pulp tissue is partially damaged or exposed, a "pulpotomy" or "pulp capping" material is required to maintain the vitality of the pulp. Such materials should be biocompatible, nontoxic, and bioactive. Furthermore, suitable pulpotomy or pulp capping materials provide the regeneration of surrounding tissues and dentine.

In certain embodiments, the filling and/or sealing dental materials disclosed herein can be applied to a wet environment of the oral cavity and offer an acceptable setting in the presence of moisture and blood. Some features of the disclosed materials may provide better wetting, penetration, filling and/or sealing than prior art materials and therefore facilitated ease of administration at the moist environment of mouth or bone. This is particularly important when the material is employed for root-end filling where bleeding is often difficult to control. More specifically, the disclosed bone/endodontic materials are capable of providing improved bioactivity, induction of mineralization, and bioadhesion to the target soft/hard tissues. The disclosed medical/dental materials provide improved handling, which facilitates clinical administration, even in target sites with complicated surgical access.

The ratio of liquid to powder phase within the disclosed materials may be within a range of 0.5 to 100 weight percent. The components in the powder phase can be in various particulate forms and size including microscale, nanoscale, macroscale particles, and mixtures thereof.

In some implementations, the liquid phase may contain collagen solution, and the powder may contain calcium based mineral compounds containing DHB moieties (e.g. 3,4-dihydroxyphenethylamine). In some embodiments, the powder phase can include approximately 1-60% collagen and 40-99% calcium-based mineral by weight. The powder phase may be anhydrous, and can be rehydrated before use.

The powder phase may comprise carbonate apatite, calcium phosphate, calcium sulfate, calcium carbonate, an organic bone mineral, or a combination of these substances.

The calcium-based mineral can have particle sizes of roughly 0.1-2000 μm. The calcium-based mineral can be natural or synthetic sources.

The collagen matrix can be of various compositions. For instance, it can be composed of type I collagen solution, sponge material, fibers, cross-linked to create a three-dimensional matrix. This matrix can vary in arrangement to create a matrix with varying porosity or other physicochemical properties.

In some embodiments, the material may comprise a therapeutic compound or agent such as growth factors and stem cells to regenerate the pulp-dentin complex tissues.

In some embodiments, the disclosed materials may form an antibacterial paste to be used for root canal therapy, where the materials comprise a macromonomer or polymer component comprising DHB moieties in order to localize antibacterial agent(s) (e.g. antibacterial peptides, drugs).

In some embodiments, the endodontic filler compound may be prepared by mixing the collagen, $CaCl_2$, $K_2HPO_4$ solutions just before use. The collagen solution may be composed of materials comprising DHB moieties (e.g. 3,4-dihydroxyphenethylamine). The mole ratio of calcium to phosphate in the composition should be between 2:1 and 1:1 in order to simulate the theoretical ratio of calcium to phosphate in hydroxyapatite crystals. The resulting composition is a highly viscous material, and forms a gel within less than an hour at 37° C.

The collagen solution may be dialyzed against a 0.115 M phosphate buffer with a pH of 7.6 at 4° C. for 24 hours to raise the pH of the collagen to physiologic pH.

In an embodiment, a set accelerator (e.g. $CaCl_2$) can be added to the composition. The set accelerator can be in the liquid phase in an amount up to 40% in weight to the weight of the liquid phase.

In some embodiments, the liquid phase of the compound may be consisted of a macromonomer or polymer as viscosity enhancer substance, and the powder phase comprise one or more of: Portland cement, a compound comprising DHB moieties, and a radiopaque substance. The Portland cement may be selected from any appropriate grade of Portland cements. The basic components of Portland cement are usually silica ($SiO_2$), lime ($CaO$), alumina ($Al_2O_3$) and iron oxide ($Fe_2O_3$). A particular example of raw materials in Portland cement used for the presently disclosed subject matter has the following formulation suggested in (U.S. Pat. Nos. 5,415,547 and 5,769,638): $SiO_2$: 21%, $Al_2O_3$: 4%, $Fe_2O_3$: 5%, $CaO$: 65%, $MgO$: 2%, $SO_3$: 2.5%, Alkalis ($Na_2O$, $K_2O$): 0.5%. The cement consists principally of tricalcium silicate, dicalcium silicate, tricalcium aluminate and tetracalcium aluminoferrite.

The materials may comprise a viscosity enhancing substance. The viscosity enhancing substance may be polymeric (e.g. poly(vinyl alcohol) (PVA), cellulose, cellulose derivatives, polyethylene oxide, natural gums) and may comprise DHB moieties.

The viscosity enhancing substance may be present at a preferable concentration range, for example, 1 to 3% of the powder component of the composite material. It should be noted that any suitable viscosity enhancing material may be used for the presently disclosed subject matter. The viscosity enhancer may be incorporated into either the liquid phase and/or powder phase. In some embodiments, the polymer is present in the powder phase in an amount ranging from 0.5 to 50% in weight to the weight of the powder phase.

In a preferred embodiment, the polymer to be functionalized with DHB moieties is selected from the group comprising polyvinyl alcohols, polyvinyl-pyrrolidone, partially hydrolyzed polyvinyl acetates, polycarboxylates, polyacrylic acid, polymethacrylic acid, acrylic based polymers, functionalized alginate and mixtures thereof. Cellulose derivatives include but are not limited to carboxymethylcellulose, hydroxypropylmethylcellulose.

In some embodiments of the disclosed materials, the materials further comprise Gutta-Percha point material, for example, where the materials are used as dental filling materials (e.g., such as for root canal therapy).

In some embodiments, the construct used for apexification or apexogenesis or pulpotomy may comprise one or more of a calcium salt, a phosphate salt, a buffered solution of colloidal collagen, or another bioactive agent.

Example 3.1

In one example, the filling dental construct was prepared by mixing 2 ml collagen (1 wt %), 1 ml $CaCl_2$ (0.4 M), 1 ml $K_2HPO_4$ (0.36 M) solutions. The collagen solution was containing 3,4-dihydroxyphenethylamine (0.1 wt %). The PH of the solution was adjusted to the physiological pH (7.4).

Example 3.2

In one example, the powder phase in comprising tricalcium phosphate and poly (3,4-dihydroxyphenylalanine) nanoparticles, and the liquid phase is collagen solution (1 wt %). The liquid and powder phase are mixed in 1:1 weight ratio. The final pH of the construct in adjusted to 7.4.

Nanoparticles comprising DHB moieties were synthesized through the following procedure: 3, 4-dihydroxyphenylalanine (10 mM) was dissolved in a buffer solution (pH 8.5) containing 500 mM sodium chloride. The solution was allowed to react for 16 h with shaking in room temperature. The solution was then centrifuged and freeze dried.

Example 3.3

The powder phase in the dental construct to be used for root canal repair is consisted of white Portland cement 90 percent and bismuth oxide 10 weight percent in powder weight. The liquid phase is prepared by dissolving of 5 weight percent carboxymethylcellulose functionalized DHB moieties in distilled water. The powder and liquid phase are then mixed in 3:1 weight ratio.

Example 3.4

The powder phase in the dental construct to be used for root canal repair includes hydroxyapatite powder (particle size<100 um), bismuth oxide, and photocrosslinkable alginate (methacrylated alginate, AlgMA) modified with DHB moieties, which was synthesized in two steps as described below. The liquid phase is distilled water. The powder and liquid phase are then mixed in variable compositions as summarized in the table below.

| Hydroxyapatite (wt %) | Bismuth oxide (wt %) | Modified AlgMA (wt %) | Powder:liquid ratio |
|---|---|---|---|
| 35 | 10 | 55 | 1:5 |
| 65 | 10 | 25 | 1:3 |
| 70 | 10 | 20 | 1:2 |
| 85 | 10 | 5 | 1:1 |
| 85 | 10 | 5 | 3:1 |

The photocrosslinkable alginate (AlgMA) was prepared through esterification of its hydroxyl groups. 500 mg of alginate powder was dissolved in 50 mL of deionized water. Methacrylic anhydride (10 g) was added to the chilled alginate solution. The pH of solution was adjusted to 5 using sodium hydroxide solution and allowed to react for one day at 0-4° C. The resultant mixture was dialyzed in sterile water for two days to remove unreacted reagents. The purified solution was precipitated in cold ethanol and dried in a vacuum oven.

DHB moieties were conjugated onto photocrosslinkable alginate (modified AlgMA) chains through carbodiimide chemistry. The amine group of 3,4-dihydroxyphenethylamine conjugated to the carboxyl group of the alginate backbone. Purified alginate was dissolved in a 50 ml phosphate buffer solution (pH 5.0) at a concentration of 0.5 weight percent, and then followed by the addition of the cross-linking agents (0.25 g 1-ethyl-3-(3-dimethylaminopropyl) carbodiimide and 0.40 g N-hydroxysuccinimide). After stirring the reactant mixture for 30 min, 0.25 g of 3,4-dihydroxyphenethylamine hydrochloride was added for the conjugation with alginate. The conjugation proceeded overnight at room temperature under mild stirring. Finally, the resultant mixture was dialyzed against distilled water to remove impurities, and then freeze-dried.

In certain embodiments, the hydroxyapatite may be replaced with other mineral compounds including but not limited to Portland cement, tricalcium phosphate, MTA, bioactive glass, or mixtures thereof.

In certain embodiments, the modified alginate may be replaced by other modified polymers (e.g. chitosan, hyaluronic acid, and gelatin) and mixtures thereof.

Example 3.5

In one example, the powder phase was Portland cement comprising modified alginate with DHB moieties per the table below.

| Portland Cement (wt %) | Bismuth oxide (wt %) | Modified alginate (wt %) | Powder:liquid ratio |
|---|---|---|---|
| 35 | 10 | 55 | 1:5 |
| 65 | 10 | 25 | 1:3 |
| 70 | 10 | 20 | 1:2 |
| 85 | 10 | 5 | 1:1 |
| 85 | 10 | 5 | 3:1 |

Modified alginate was synthesized through the following procedure. DHB moieties were conjugated onto alginate chains through carbodiimide chemistry. The amine group of 3,4-dihydroxyphenethylamine conjugated to the carboxyl group of the alginate backbone. Purified alginate was dissolved in a 50 ml phosphate buffer solution (pH 5.0) at a concentration of 0.5 weight percent, and then followed by the addition of the cross-linking agents (0.25 g 1-ethyl-3-(3-dimethylaminopropyl) carbodiimide and 0.40 g N-hydroxysuccinimide). After stirring the reactant mixture for 30 min, 0.25 g of 3,4-dihydroxyphenethylamine hydrochloride was added for the conjugation with alginate. The conjugation proceeded overnight at room temperature under mild stirring. Finally, the resultant mixture was dialyzed against distilled water to remove impurities, and then freeze-dried.

Example 3.6

In one example the formulation of the construct are as follows; Powder phase: Portland cement 60 wt %, calcium carbonate 10 wt %, bismuth oxide 10 wt %, polycarboxylate functionalized with DHB moieties 5 wt %, calcium chloride 10 wt %; The liquid phase is composed of 15 wt % polycarboxylate functionalized with DHB moieties in water.

Example 4: Construct 4: Integrated Heterophasic Scaffolds

In certain embodiments of the presently disclosed materials, the material is a hybrid multiphasic construct for single or multi-tissue regeneration or healing, which construct comprises the following phase/parts: (1) a scaffold phase that acts as a supportive phase (e.g. comprising and/or prepared from 3D-printed scaffold material, porous titanium material, bioceramic scaffold material), where preferably the scaffold phase is capable of accommodating (e.g. via immobilization, conjugation, encapsulation) therapeutic or bioactive molecules (e.g., antibacterial agents, therapeutic drugs, growth factors); (2) another phase which acts as a biomaterial matrix (e.g., comprising and/or prepared from freeze-dried collagen sponge material, and/or decellularized bone granule material) which biomaterial matrix optionally may be embedded partially or throughout the supportive phase and may accommodate cells or other bioactive agents; and optionally (3) a third phase which may act as a barrier to prohibit or control infiltration of unwanted agents (e.g. water, cells, bacteria) and/or may provide a platform for regeneration of a different desirable tissue. Optionally, one or more of the phases of the material may incorporate DHB moieties or other chemicals.

Tissue engineering aims to regenerate various tissues through combining a triad of elements: scaffold, growth factors and stem/progenitor cells. Multiphasic constructs act as templates for tissue regeneration, to guide the growth of new tissue. A major challenge in fabricating multiphasic scaffolds is obtaining adhesion between the various parts that may be consist of different materials. In this disclosure, by using incorporations of DHB moieties or other chemicals the attachment between different phases are provided. Porosity and pore size are considerations vital to the design, and ultimately fabrication of scaffolds for tissue engineering. Depending on the biomaterial used to fabricate the scaffold, porosity is most commonly created via salt leaching, gas foaming, layer-by-layer (LbL) assembly, phase separation, freeze-drying, electrospinning, microsphere sintering, 3D-printing or other additive manufacturing techniques. The hierarchical structure of native tissues requires various methods to fabricate scaffolds with micro- to macro-scale pore sizes, and anisotropic pore distribution, while tailoring the spatial composition and geometry. On the other hand, various features of multiphasic scaffolds such as pore size and topography have been found to profoundly affect the cell attachment, migration, proliferation, and differentiation, and cell-cell interactions. Each conventional scaffold fabrication technique by itself, albeit providing various topographical cues, is unable to precisely provide desired porosity, mechanical properties, pore size, geometry, and interconnectivity. While nano/microscale features within the scaffold are intended to mimic the native extracellular matrix arrangement, macroscale porosity promote tissue ingrowth and vascularization. Hence, multiple fabrication methods should be employed to construct scaffold matrix with well-defined porosity and organized structures.

Construct 4. Integrated Heterophasic Scaffolds

Example 4.1

In some embodiments, the adhesion/integration between 3D-printed polylactic acid (PLA) scaffold (support phase)

and freeze-dried collagen (matrix phase) was provided by functionalization of either PLA or collagen phase. The functionalization with DHB may also provide incorporation of bioactive agent such as growth factors.

In this example, the PLA scaffolds prepared by 3D printing method were embedded with porous collagen matrix. The surface of PLA scaffolds was treated in a two steps method. First, scaffolds were treated with soaking in 0.1 wt. % neutral 3,4-dihydroxyphenethylamine solution for 12 h at 37° C. followed by washing with distilled water. Subsequently the scaffolds were immersed in 0.5 wt. % neutral 3,4-dihydroxyphenethylamine solution for 12 h at 37° C. followed by washing with distilled water. The acidic collagen solution was then filled into the porosity of the PLA scaffolds and freeze-dried. The collagen matrix was cross-linked using carbodiimide chemistry. Subsequently, BMP-2 solution was added to the integrated biphasic construct. The obtained in vitro results showed that the untreated PLA scaffolds could not provide integration with the collagen matrix and delaminated in aqueous environment.

In certain embodiments, the scaffolds materials (support phase) may be selected from metallic (e.g. Titanium, Alloys), polymeric (e.g. PLA, PCL, PDLA, PEEK), ceramic (e.g. Calcium phosphate, calcium silicate, zirconium oxide) or mixtures thereof. The DHB moieties may be incorporated into the support phase in various methods including but not limited to surface adsorption, particle incorporation or polymer grafting. In certain embodiments, the DHB moieties can be employed for surface modification of implants and/or to incorporate bioactive agent (e.g. growth factors) to the polymeric, metallic or ceramic implants (PEEK, Titanium, Zirconia) via various methods including but not limited to layer by layer assembly.

REFERENCES

1. Hutmacher, D. W., 2000. Scaffolds in tissue engineering bone and cartilage. Biomaterials, 21(24). pp. 2529-2543.
2. Griffith, L. G. and Naughton, G., 2002. Tissue engineering-current challenges and expanding opportunities. Science, 295(5557), pp. 1009-1014.
3. Lu, H. H. and Jiang, J., 2005. Interface Tissue Engineering and the Formulation of Multiple-Tissue Systems. In Tissue Engineering I (pp. 91-111). Springer Berlin Heidelberg.
4. Williams, R. C., 1990. Periodontal disease. New England Journal of Medicine, 322(6), pp. 373-382.
5. Bartold P M, McCulloch C A, Narayanan A S, Pitaru S (2000). Tissue engineering: a new paradigm for periodontal regeneration. Periodontol 2000 24:253-269.
6. Chen J, Chen H, Li P, Diao H, Zhu S, Dong L, et al. (2011). Simultaneous regeneration of articular cartilage and subchondral bone in vivo using MSCs induced by a spatially controlled gene delivery system in bilayered integrated scaffolds. Biomaterials 32:4793-4805.
7. Darby I B, Morris K H (2013). A systematic review of the use of growth factors in human periodontal regeneration. J Periodontol 84:465-476.
8. Harley B A, Lynn A K, Wissner-Gross Z, Bonfield W, Yannas I V, Gibson L J (2010). Design of a multiphase osteochondral scaffold: I. Fabrication of layered scaffolds with continuous interfaces. J Biomed Mater Res A 92:1078-1093.
9. Hynes K, Menicanin D, Gronthos S, Bartold P M (2012). Clinical utility of stem cells for periodontal regeneration. Periodontol 2000, 59:203-227.
10. Iwata T, Yamato M, Tsuchioka H, Takagi R, Mukobata S, Washio K, et al. (2009). Periodontal regeneration with multi-layered periodontal ligament-derived cell sheets in a canine model. Biomaterials 30:2716-2723.
11. Wang W, Li B, Yang J, Xin L, Li Y, Yin H, et al. (2010). The restoration of full-thickness cartilage defects with BMSCs and TGF-beta 1 loaded PLGA/fibrin gel constructs. Biomaterials 31:8964-8973.
12. Park, C. H., Rios, H. F., Jin, Q., Sugai, J. V., Padial-Molina, M., Taut, A. D., Flanagan, C. L., Hollister, S. J. and Giannobile, W. V., 2012. Tissue engineering bone-ligament complexes using fiber-guiding scaffolds. Biomaterials, 33(1), pp. 137-145.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

We claim:
1. An integrated heterophasic biomedical construct for multi-tissue regeneration or healing at a multi-tissue interface comprising
    (a) a supportive phase capable of holding sutures, wherein the supportive phase comprises and/or is prepared from 3D-printed materials, titanium mesh materials, bioceramic scaffold materials, biocompatible glue materials, polymeric film materials, and/or electrospun mat materials; and
    (b) a matrix phase, wherein the matrix phase comprises and/or is prepared from freeze-dried collagen sponge material,
    wherein the supportive phase and/or the matrix phase comprise hydroxylated aromatic moieties, wherein the hydroxylated aromatic moieties adhere the supportive phase and the matrix phase together, wherein the hydroxylated aromatic moieties adhere the biomedical construct to soft and hard tissue, wherein the biomedical construct is capable of adhering to both soft and hard tissue at a multi-tissue interface, and wherein the biomedical construct provides a surface for cell growth, and
    wherein the supportive phase is in contact with the hard tissue and the matrix phase is in contact with the soft tissue.

2. The biomedical construct of claim 1, wherein the hydroxylated aromatic moieties are dihydroxybenzene (DHB) moieties.

3. The biomedical construct of claim 2, wherein the DHB moieties are incorporated into one or more of the phases in a form or manner selected from a salt form, as part of polymerized particles, via in-situ polymerization, via photo-polymerization, via functionalization to polymer chains, and via surface modification of particles, and the DHB moieties improve bioactivity of the constructs.

4. The biomedical construct of claim 1, wherein the hydroxylated aromatic moieties are 1,2-DHB moieties.

5. The biomedical construct of claim 1, wherein the supportive phase has bioadhesive properties whereby the supportive phase is capable of accommodating therapeutic or bioactive molecules.

6. The biomedical construct of claim 1 further comprising a third phase comprising polycaprolactone film and/or collagen film.

7. The biomedical construct of claim 1, wherein the biomedical construct is material for bone/endodontic fitting and/or sealing.

8. The biomedical construct of claim 7, wherein the biomedical construct comprises: (1) a liquid phase which functions as a binder phase; and (2) a powder phase which functions as a matrix.

9. The biomedical construct of claim 8, wherein the liquid phase comprises macromonomers and/or polymers.

10. The biomedical construct of claim 8, wherein the powder phase comprises calcium or a calcium salt such as calcium oxide, calcium silicate, calcium phosphate, and/or calcium aluminate.

11. The biomedical construct of claim 8, further comprising a spongy form as a third phase, which optionally is a collagen sponge.

12. The biomedical construct of claim 8, wherein the DHB moieties are incorporated in the liquid phase and/or powder phase in a form or manner selected from a salt form, as part of polymerized particles, via in-situ polymerization, via photo-polymerization, via functionalization to polymer chains, and via surface modification of particles, and the DHB moieties improve bioactivity of the construct.

13. The biomedical construct of claim 1, wherein the biomedical construct is a microcarrier for dynamic cell expansion in vitro and/or a microscaffold for tissue regeneration.

14. The biomedical construct of claim 13, comprising microparticles which act as the matrix phase and which may accommodate cells or other bioactive agents.

15. The biomedical construct of claim 14, wherein the microparticles comprise and/or are formed from polymeric particles, ceramic particles, polymer/ceramic hybrid particles, and/or decellularized bone granules.

16. The biomedical construct of claim 1, wherein the supportive phase comprises a polymer scaffold selected from polycaprolactone (PCL), poly D-lactic acid (PDLA), polyether ether ketone (PEEK), and polylactic acid (PLA).

17. The biomedical construct of claim 1, wherein the matrix phase is embedded partially or throughout the supportive phase and may accommodate cells or other bioactive agents.

* * * * *

UNITED STATES PATENT AND TRADEMARK OFFICE
CERTIFICATE OF CORRECTION

| | |
|---|---|
| PATENT NO. | : 12,076,422 B2 |
| APPLICATION NO. | : 16/612328 |
| DATED | : September 3, 2024 |
| INVENTOR(S) | : Lobat Tayebi et al. |

It is certified that error appears in the above-identified patent and that said Letters Patent is hereby corrected as shown below:

On the Title Page

Item (57) Abstract, Line 10, "moeities" should be --moieties--.

In the Specification

Column 10, Line 1, "(GeMA)" should be --(GelMA)--.

Column 10, Line 1, "(AgMA)" should be --(AlgMA)--.

Column 12, Line 37, "carageenan" should be --carrageenan--.

Column 23, Line 56, "pulpoomy" should be --pulpotomy--.

Signed and Sealed this
Fifth Day of November, 2024

Katherine Kelly Vidal
*Director of the United States Patent and Trademark Office*